(12) United States Patent
Bae et al.

(10) Patent No.: US 8,877,203 B2
(45) Date of Patent: Nov. 4, 2014

(54) COMPOSITION AND METHOD FOR PREVENTING AND TREATING IMMUNE-RELATED DISORDER

(75) Inventors: Yoe-Sik Bae, Busan (KR); Sang-Doo Kim, Yangsan (KR); Yoon-Keun Kim, Pohang (KR); Sung-Ho Ryu, Pohang (KR)

(73) Assignees: Postech Academy-Industry Foundation, Pohang (KR); Dong-A University Research Foundation for Industry-Academy Cooperation, Busan (KR)

( * ) Notice: Subject to any disclaimer, the term of this patent is extended or adjusted under 35 U.S.C. 154(b) by 219 days.

(21) Appl. No.: 12/740,729

(22) PCT Filed: Nov. 3, 2008

(86) PCT No.: PCT/KR2008/006468
§ 371 (c)(1),
(2), (4) Date: Apr. 30, 2010

(87) PCT Pub. No.: WO2009/057982
PCT Pub. Date: May 7, 2009

(65) Prior Publication Data
US 2010/0249018 A1    Sep. 30, 2010

Related U.S. Application Data

(60) Provisional application No. 60/984,729, filed on Nov. 2, 2007.

(51) Int. Cl.
*C07K 7/06* (2006.01)
*A61K 31/19* (2006.01)
*A61K 38/08* (2006.01)

(52) U.S. Cl.
CPC . *A61K 38/08* (2013.01); *C07K 7/06* (2013.01); *A61K 31/19* (2013.01)
USPC ..................................................... 424/184.1

(58) Field of Classification Search
None
See application file for complete search history.

(56) References Cited

U.S. PATENT DOCUMENTS

| 6,808,877 B2 * | 10/2004 | Wang et al. | 435/5 |
| 7,030,090 B2 * | 4/2006 | Ryu et al. | 514/2.4 |
| 2003/0224987 A1 * | 12/2003 | Ryu et al. | 514/12 |

FOREIGN PATENT DOCUMENTS

| JP | 2005-521388 | 7/2005 |
| KR | 10-2001-0076648 | 8/2001 |
| KR | 10-0630489 | 9/2006 |

OTHER PUBLICATIONS

Kim, H. et al., "Granulocyte function is stimulated by a novel hexapeptide WKYMVm, inchemotherapy-treated cancer patients", Exp. Hematol., 2006, vol. 34, pp. 407-413.
Bae, Y.S., et al., The synthetic chemoattractant peptide, Trp-Lys-Tyr-Met-Val-d-Met, enhances monocyte survival via PKC-dependent Akt activation, J. Leukoc. Biol. 71:329-338, Feb. 2002.
Riedemann, Novel strategies for the treatment of sepsis, N.C., et al., Nat. Med. 9:517-524, 2003.
Cohen, J. , Adjust therapy in sepsis: a critical analysis of the clinical trial programme, Br. Med. Bull. 55:212-225, 1999.
Dhainaut, J.F., et al., Confirmatory platelet-acticating factor receptor antagonist trial in patients with severe Gram-negative bacterial sepsis: A phase III, randomized, double-blind, placebo-controlled, multicenter trial, Crit. Care Med. 26:1963-1971, 1998.
Fisher, C.J. et al., Recombinant Human Interleukin 1 Receptor Antagonist in the Treatment of Patients With Sepsis Syndrome, JAMA. 271:1836-1843, 1994.

* cited by examiner

*Primary Examiner* — Yunsoo Kim
(74) *Attorney, Agent, or Firm* — Lexyoume IP Meister, PLLC

(57) ABSTRACT

The present invention relates to an immunoregulating agent comprising a peptide, a pharmaceutical composition and a method of preventing or treating immune-related disorder such as sever sepsis or acute respiratory distress syndrome (ARDS), and the use of peptide for anti-inflammatory agent, an antibacterial agent, or an inhibiting agent of an immune cell apoptosis.

10 Claims, 28 Drawing Sheets

COMPOSITION AND METHOD FOR PREVENTING AND TREATING IMMUNE-RELATED DISORDER

FIELD OF THE INVENTION

The present invention relates to an immune modulating agent comprising a peptide, a pharmaceutical composition and a method of preventing or treating immune-related disorders such as severe sepsis or acute respiratory distress syndrome (ARDS), and the use of peptide for anti-inflammatory agent, an antibacterial agent, or an inhibiting agent of an immune cell apoptosis.

DETAILED DESCRIPTION

FPR is a G-protein-coupled classical chemoattractant receptor found in phagocytic cells such as neutrophils, monocytes, macrophages, and dendritic cells. Three FPRs [FPR, FPR-like (FPRL)1, and FPRL2] and two FPRs (FPR1 as a counterpart for human FPR and FPR2 as a counterpart for human FPRL1) have been identified in humans and mouse, respectively. The activation of FPR family members induces leukocyte chemotactic migration and bactericidal activity via superoxide anion generation in neutrophils and monocytes. WKYMVm, a synthetic peptide capable of stimulating chemotactic migration in phagocytes, binds to members of the FPR family (FPR1 and FPR2 in mice, and FPR, FPRL1 and FPRL2 in humans) in vitro and enhances the bactericidal activity of monocytes and neutrophils via the production of superoxide anions. WKYMVm has also been found to enhance monocyte survival by blocking apoptosis (Bae, Y. S., et al., J. Leukoc. Biol. 71:329-338, 2002). Thus, this experiment investigated the therapeutic effects and functional mechanisms of the FPR agonist WKYMVm in the progression to severe sepsis after microbial infection based on the notion that the major cause of sepsis-induced mortality is uncontrolled bacterial infection and that FPR activation enhances the bactericidal activity of immune and inflammatory cells.

Recent studies indicate that sepsis-induced mortality is accompanied by an inability to regulate the inflammatory response because of substantial impairment of the innate immune system during early sepsis (i.e., during the first 6 h). In addition, excessive lymphocyte apoptosis occurs during sepsis, resulting in the clinical signs of multi-organ failure. Moreover, studies indicate that cytokine levels are markedly altered during sepsis; in particular, the levels of such pro-inflammatory cytokines as TNF-α and IL-1β are greatly increased. These findings indicate that the effective prevention of mortality by severe sepsis or septic shock requires drugs that enhance the bactericidal activity of phagocytes, inhibit the production of pro-inflammatory mediators, and prolong antigen-specific adaptive immune responses.

Many patients with severe sepsis or septic shock die despite aggressive management. One means of preventing severe sepsis is to neutralize endotoxin; however, the potential of such a target for therapeutic intervention is controversial (Riedemann, N. C., et al., Nat. Med. 9:517-524). In placebo-controlled clinical trials, monoclonal antibodies to endotoxin did not prevent the death of patients with severe Gram-negative bacterial sepsis (Cohen, J. Br. Med. Bull. 55:212-225, 1999). Other adjunctive therapies that are intended to control the inflammation regardless of the microbial stimuli, e.g., agents which directly or indirectly interfere with the activity of inflammatory mediators (e.g., platelet activating factor antagonist (Dhainaut, J. F., et al., Crit. Care Med. 26:1963-1971, 1998), recombinant IL-1β receptor antagonist (Fisher, C. J. et al., JAMA. 271:1836-1843, 1994), genetically engineered soluble receptors for TNF-α, and monoclonal antibodies to TNF-α, have not prevented the death of patients with severe sepsis or septic shock (Riedemann, N. C., et al., Nat. Med. 9:517-524, 2003).

SUMMARY OF THE INVENTION

FPR activation by WKYMVm after the induction of sepsis by CLP effectively prevented CLP-induced lethality in mice via multiple therapeutic pathways; bactericidal activity of phagocytes directly and/or IFN-γ-mediated pathway, an anti-inflammatory effect via the down-regulation of pro-inflammatory mediator production partly mediated by up-regulation of IL-17 production, and an anti-apoptotic effect on immune cells. FPR activation by WKYMVm effectively prevents the progression to severe sepsis after microbial infection via multiple pathways. Thus, FPR activation might be a novel and efficient therapeutic target for the treatment of sepsis.

The present inventors found that the activation of the formyl peptide receptor (FPR) by the peptide Trp-Lys-Tyr-Met-Val-D-Met (WKYMVm) protected against death, inhibited lung inflammation, blocked immune cell apoptosis, and enhanced bactericidal activity and completed this invention.

The object of the present invention is to provide an immunoregulating agent comprising a peptide consisting of an amino acid sequence of Trp-Lys-Tyr-Met-Val-D-Met (WKYMVm) as represented in SEQ ID NO:1.

Another object of the present invention is to provide a pharmaceutical composition comprising an immunoregulating agent comprising a peptide consisting of an amino acid sequence of WKYMVm, which prevents or treats severe sepsis or Acute respiratory distress syndrome (ARDS).

Further object of the present invention is to provide a pharmaceutical composition comprising the immunoregulating agent for inhibiting the reduction of splenocyte or thymocyte which is derived by severe sepsis.

Still further object of the present invention is to provide a method of regulating immune response in a subject comprising administering to said subject an immunoregulating agent comprising a peptide consisting of an amino acid sequence of WKYMVm in a therapeutically effective amount. In the method, the regulation of immune response is involved in anti-inflammatory reaction, an antibacterial reaction, an inhibition of an immune cell apoptosis, or the prevention or treatment of severe sepsis or ARDS.

BRIEF DESCRIPTION OF THE DRAWINGS

For more complete understanding of the present invention, and the advantages thereof, reference is now made to the following descriptions taken in conjunction with the accompanying drawings, in which.

DETAILED DESCRIPTION

Figure 1A:
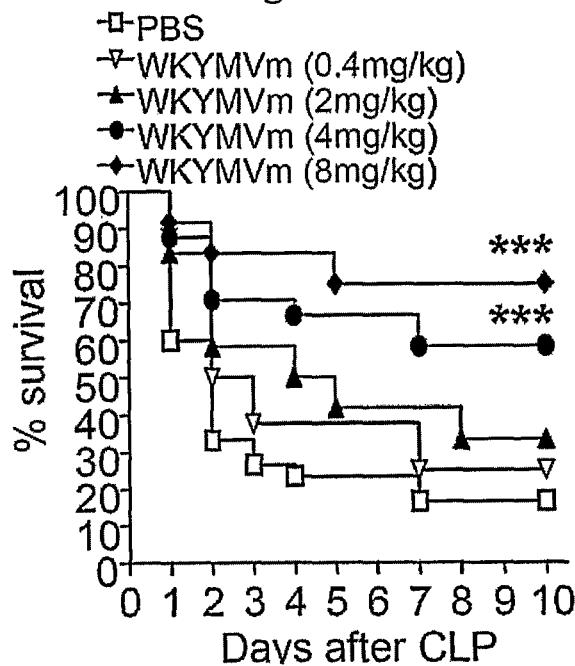
FIGS. 1a to 1f show that WKYMVm protects against sepsis-induced lethality in animal model.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

An embodiment of the present invention provides an immunoregulating agent comprising a peptide consisting of an amino acid sequence of Trp-Lys-Tyr-Met-Val-D-Met (WKYMVm) as represented in SEQ ID NO:1. An embodiment relates to a method of regulating immune response in a subject comprising administering to said subject an immunoregulating agent comprising a peptide consisting of an amino acid sequence of WKYMVm in a therapeutically effective amount.

Figure 1B:
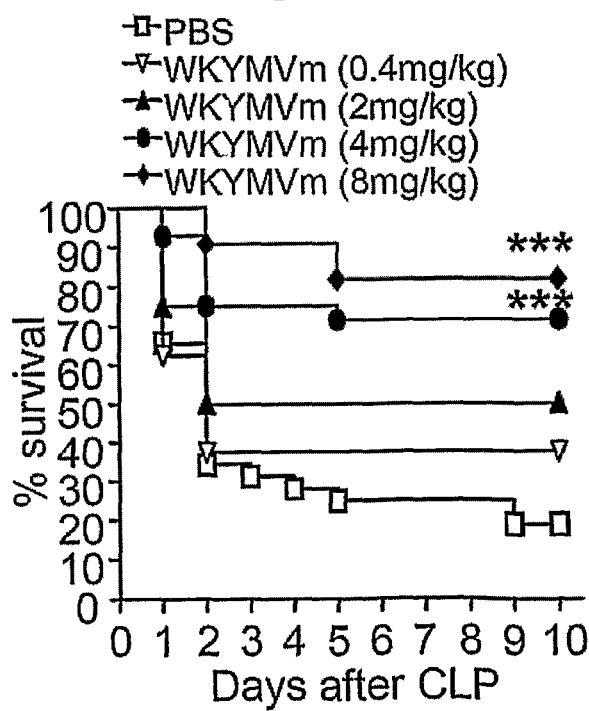

The WKYMVm peptide binds and activates Formylpeptide receptor 1 (FPR 1) and Formylpeptide receptor 2 (FPR 2) in mouse, and FPR, FPRL1 or FPRL2 in human, thereby regulating the immune response in subject. Because WKYMVm is reported to bind FPR family receptors, the therapeutic effect of other FPR ligands was evaluated, but the WKYMVm peptide had no therapeutic effect (FIG. 1G).

In addition, the peptide decreases the expression of inflammatory cytokine which is Interleukin-1β (IL-1β), Tumor necrosis factor-α (TNF-α), or Interleukin-6 (IL-6), increases the expression of Th1 cytokine which is Interferon-γ (IFN-γ), Interleukin-2 (IL-2), or Interleukin-12 (IL-12). The peptide increases the expression of Interleukin-17 (IL-17), and the expression of anti-inflammatory cytokines which are transforming growth factor-β (TGF-β) or Interleukin-10 (IL-10).

The WKYMVm peptide is used for anti-inflammatory agent, because the peptide down-regulates the production of pro-inflammatory cytokines and FPR activation exerts its therapeutic effects by preventing acute inflammation via the direct inhibition of pro-inflammatory cytokine production.

The regulation of immune response according to the present invention also includes an inhibition of an immune cell apoptosis.

The FPR activation by WKYMVm affects bacterial clearance from peritoneal fluid, and enhances $H_2O_2$ production, which was associated with enhanced bacterial clearance. Thus, the WKYMVm peptide is used for anti-bacterial agent. FPR activation by WKYMVm after the induction of sepsis by CLP effectively prevented CLP-induced lethality in mice via multiple therapeutic pathways; bactericidal activity of phagocytes directly and/or IFN-γ-mediated pathway, an anti-inflammatory effect via the down-regulation of pro-inflammatory mediators, and an anti-apoptotic effect on immune cells. FPR activation by WKYMVm (SEQ ID NO:1) effectively prevents the progression to severe sepsis after microbial infection via multiple pathways. Thus, FPR activation might be a novel and efficient therapeutic target for the treatment of severe sepsis and Acute respiratory distress syndrome (ARDS). The anti-inflammatory agent, an antibacterial agent, or an inhibiting agent of an immune cell apoptosis of WKYMVm peptide are largely involved in the prevention and treatment effect of sever sepsis, by decreasing the expression of inflammatory cytokine and increasing the Th1 cytokine. In addition, the immunoregulating activities such as increased expression of IL-10 and anti-inflammatory cytokines of TFG-β and IL-10 of WKYMVm peptide is largely involved in the prevention and treatment of ARDS.

Figure 1C:
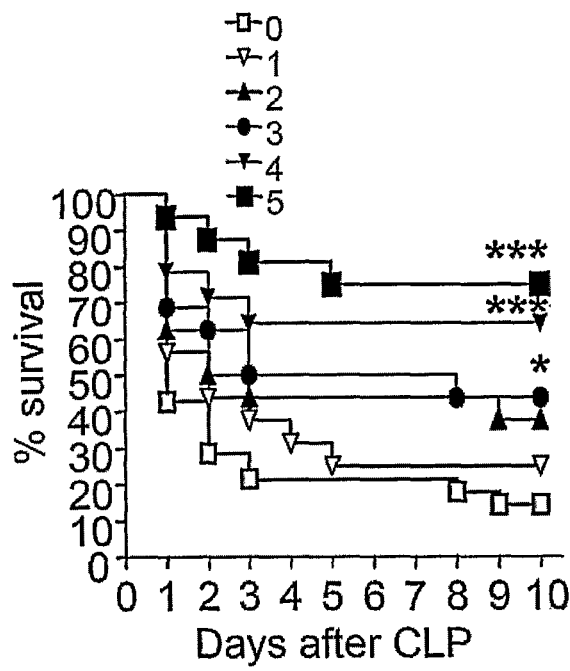
Figure 1D:
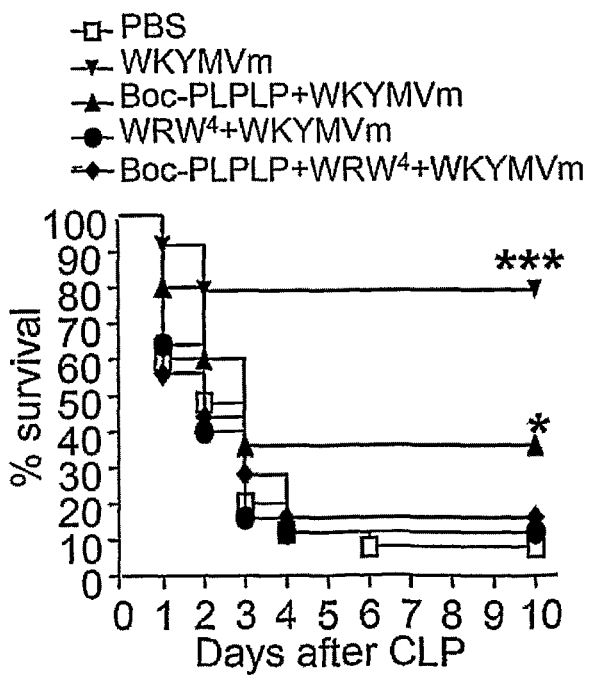
Figure 1E:
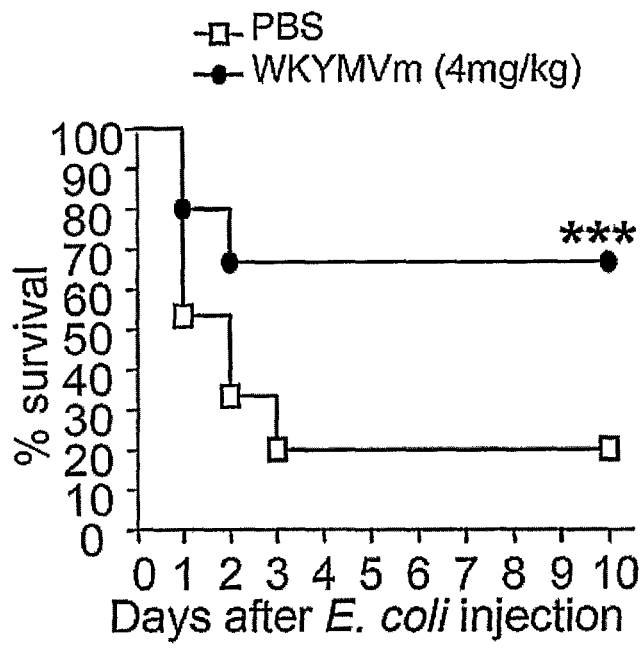
Figure 1F:
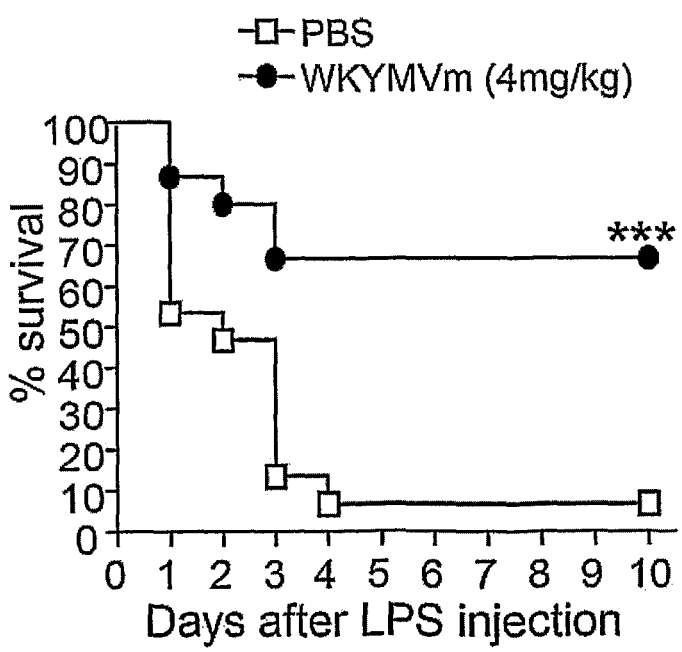
Figure 1G:
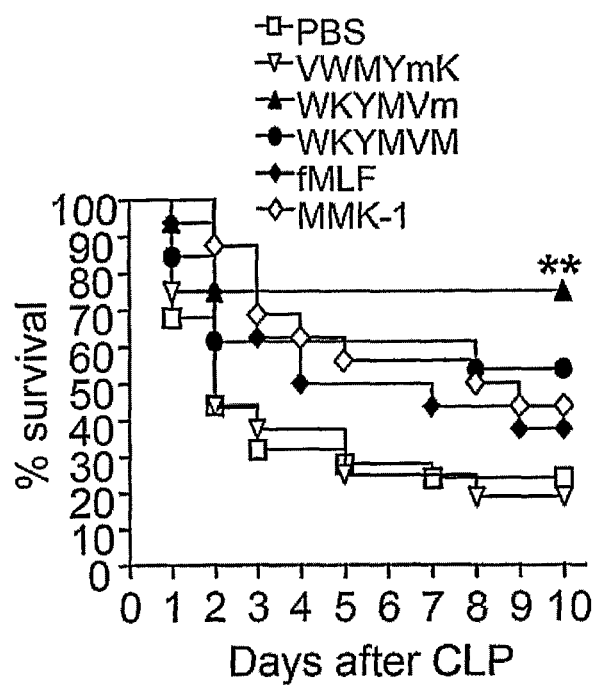
FIGS. 1g to 1h show the therapeutic effect of WKYMVm on other FPR ligands and of WKYMVm analogs.
Figure 1H:
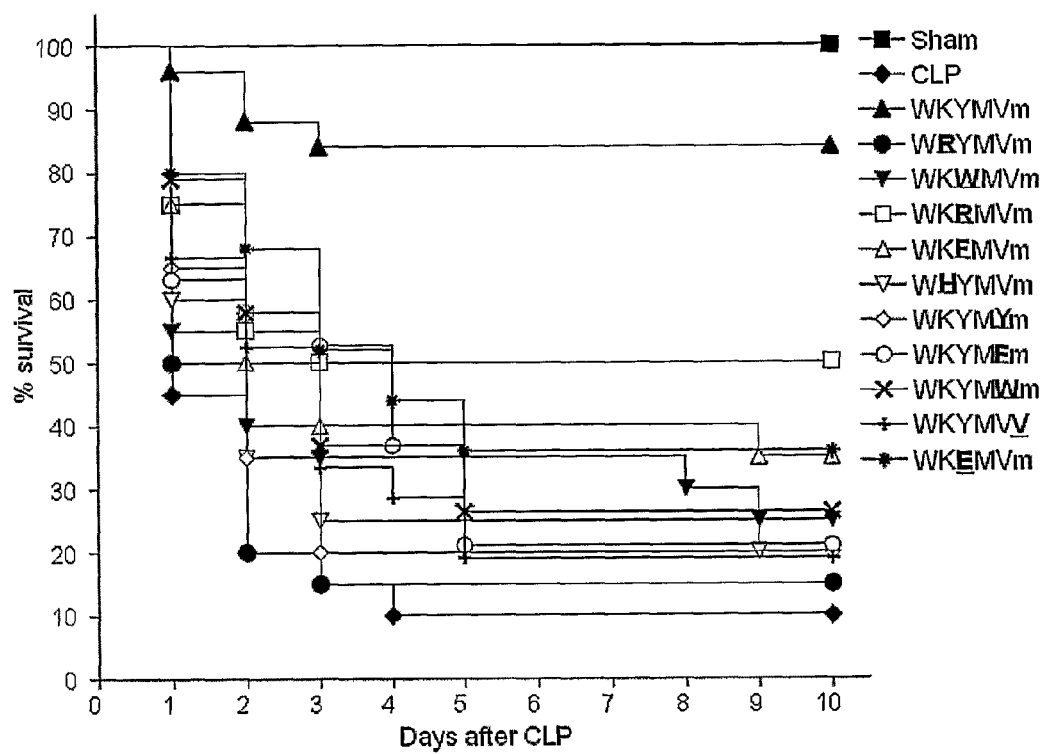

Unlike the WKYMVm peptide, the analogs of WKYMVm such as WRYMVm(SEQ ID NO:2), WKWMVm(SEQ ID NO:3), WKRMVm(SEQ ID NO: 4), WKFMVm(SEQ ID NO:5), WHYMVm(SEQ ID NO:6), WKYMYm(SEQ ID NO:7), WKYMFm(SEQ ID NO:8), WKYMWm(SEQ ID NO:9), WKYMVV(SEQ ID NO:10), or WKEMVm(SEQ ID NO:11) had no therapeutic effects on experimental sepsis (FIG. 1h).

Preferably, the WKYMVm peptide is administered in an amount of 0.0064 to 6.4 mg/kg·day in human, and more preferably 0.064 to 0.64 mg/kg·day. In the administered amount ranges, the WKYMVm peptide has more notable therapeutic effect in CLP mouse model than the analogs of WKYMVm.

The composition comprising the peptide as an active ingredient can include more than one kind of pharmaceutical diluent, selected from the group consisting of saline, buffered saline, dextrose, water, glycerol, and ethanol, but the diluent is not limited thereto.

It should be understood that the amount of the active ingredient actually administered ought to be determined in light of various relevant factors, including the condition to be treated, the severity of the patient's symptoms, co-administration with other drugs (e.g., chemotherapeutic agents), age, sex, body weight of the individual patient, food, dosing time, the chosen route of administration, and the ratio of the composition. The composition may be administrated in a single or in 1-3 divided doses per day, and preferably may be administered in a twice daily at a 12 hours interval, even though the dose and route of administration are adjusted to the type and severity of disease.

The composition comprising the peptide of the present invention can be administered via oral or parenteral routes. Parenteral dosing means the administration of a drug through a route other than oral, which includes rectal, intravenous, intraperitoneal and intramuscular, intra-arterial, transdermal, nasal, inhalation, ocular, and subcutaneous introduction.

Pharmaceutical formulations containing the peptide may be prepared in any form, such as oral dosage form, injectable solution, or topical preparation. The formulation can be preferably prepared for oral and injectable administration (true solution, suspension, or emulsion) and most preferably in oral form such as tablet, capsule, soft capsule, aqueous medicine, pill, granule, and the like.

In preparing the formulation, the peptides are filled in a soft capsule without any excipient, or formed as an appropriate formulation after mixing or diluting with a carrier. Examples of suitable carriers are starches, water, saline, Ringer's solution, dextrose, etc.

FPR activation by WKYMVm after the induction of sepsis by CLP effectively prevented CLP-induced lethality in mice via multiple therapeutic pathways; bactericidal activity of phagocytes directly and/or IFN-γ-mediated pathway, an anti-inflammatory effect via the down-regulation of pro-inflammatory mediators, and an anti-apoptotic effect on immune cells. FPR activation by WKYMVm effectively prevents the progression to severe sepsis after microbial infection via multiple pathways. Thus, FPR activation might be a novel and efficient therapeutic target for the treatment of sepsis.

Severe sepsis, a principal cause of death in intensive care units, occurs when host immune defenses fail to combat invading microbes. Here, the activation of the formyl peptide receptor (FPR) by the peptide WKYMVm protected against death, inhibited lung inflammation, blocked immune cell apoptosis, and enhanced bactericidal activity in a cecal ligation and puncture (CLP) sepsis mouse model. FPR activation by WKYMVm enhanced the bactericidal activity and hydrogen peroxide production of mouse neutrophils in vitro. FPR activation also enhanced the production of IFN-γ in CLP mice. The therapeutic and bactericidal effects of FPR activation were partly reversed in IFN-γ-deficient mice, whereas target organ inflammation was not. In contrast, FPR activation inhibited TNF-α and IL-1β production in CLP mice. Moreover, FPR activation inhibited the production of pro-inflammatory mediators induced by LPS, a key pathogen-associated molecular pattern in Gram negative bacteria. Finally, FPR activation inhibited CLP-induced immune cell apoptosis, which did not occur in CLP-induced IFN-γ-deficient mice. These results suggest that the activation of FPR effectively prevents progression to severe sepsis following microbial infection via multiple pathways.

The down-regulation of immunity that accompanies sepsis is related to the development of lymphocyte apoptosis; thus, the inhibition of sepsis-induced lymphocyte apoptosis is a good therapeutic target. FPR activation by WKYMVm may be a superior therapeutic approach. The experiments in vitro and in vivo demonstrate that FPR activation inhibits LPS-induced pro-inflammatory cytokine production. These findings suggest that the FPR activation exerts its therapeutic effects by preventing acute inflammation via the direct inhibition of pro-inflammatory cytokine production. This indicates that FPR activation by WKYMVm may be superior to blocking individual pro-inflammatory mediators in the treatment of sepsis.

The present invention is further explained in more detail with reference to the following examples. These examples, however, should not be interpreted as limiting the scope of the present invention in any manner.

EXAMPLE 1

1-1. Therapeutic Effects of WKYMVm in CLP Mouse Model

Male WT ICR mice and IL-12R 2-, IFN-γ-deficient, and WT C57BL/6 mice (kindly donated from Y. C. Sung, POSTECH, Republic of Korea) were used for experimental sepsis model, as previously described (Yan, J. J., *Nat. Med.* 10:161-167, 2004). All experiments involving animals adhered to the guidelines and received the approval of the Institutional Review Committee for Animal Care and Use at Dong-A University. For CLP, mice were anesthetized with pentothal sodium (50 mg/kg, intraperitoneal) and a small abdominal midline incision was made to expose the cecum. The cecum was then ligated below the ileocecal valve, punctured twice through both surfaces (or once for the measurement of cytokine production) using a 22-gauge needle and the abdomen was closed. Sham CLP mice were subjected to the same procedure, but without ligation and puncture of the cecum. Survival was monitored once daily for 10 days.

To investigate whether WKYMVm has a therapeutic effect on experimental sepsis, CLP was performed on albino ICR (Institute of Cancer Research) mice, and their survival was monitored for up to 10 days. Within 2 days after CLP, mouse mortality dramatically increased (FIG. 1a). Various doses of WKYMVm were injected subcutaneously four times into CLP mice at 2, 14, 26, and 38 h post-CLP.

To examine the effect of WKYMVm treatment, mice were injected subcutaneously with various doses of the peptide or with PBS as a negative control beginning 2 h after CLP. Treatment with 4 or 8 mg/kg WKYMVm dramatically increased mouse survival compared to the PBS-injected controls (FIG. 1a). When WKYMVm was injected 10 h post-CLP, the therapeutic effect was similar to that observed following injection of the peptide 2 h post-CLP (FIG. 1b). Various doses of WKYMVm were injected subcutaneously four times into CLP mice at 10, 22, 34, and 48 h post-CLP.

In terms of injection frequency, survival was greatly improved when 4 mg/kg WKYMVm was injected 2 h post-CLP and at 12 h intervals three or four additional times (FIG. 1c). CLP mice were given zero, one, two, three, four, or five injections of WKYMVm (4 mg/kg, subcutaneous). Given these results, the subsequent experiments were performed in CLP mice using 4 mg/kg WKYMVm beginning 2 h after CLP and at 12 h intervals three additional times.

To evaluate the roles of FPR1 and FPR2, an FPR1 antagonist [N-t-butoxycarbonyl-Phe-Leu-Phe-Leu-Phe (Boc-PLPLP) (SEQ ID NO:12)] (La, M., et al., *FASEB J.* 15:2247-2256) and an FPR2 antagonist [Trp-Arg-Trp-Trp-Trp-Trp; WRWWWW (WRW$^4$) (SEQ ID NO:13)] (Bae, Y. S et al., *J. Immunol.* 173:607-614.) were administered prior to WKYMVm treatment in CLP mice. The therapeutic effects of WKYMVm were completely reversed by pre-treatment with WRW$^4$, but only partly reversed by Boc-PLPLP (FIG. 1d). Boc-PLPLP (4 mg/kg), WRW$^4$ (4 mg/kg), or Boc-PLPLP (4 mg/kg)+WRW$^4$ (4 mg/kg) was injected subcutaneously 2 h before CLP. After CLP, Boc-PLPLP (4 mg/kg) or WRW$^4$ (4 mg/kg) was injected subcutaneously four times at 12-h intervals 2 h before WKYMVm treatment (4 mg/kg, subcutaneous).

Statistical analysis. Survival data were analyzed using the log-rank test. All other data were evaluated using ANOVA. The Bonferroni test was used for post hoc comparisons and statistical significance was set a priori at $P<0.05$.

1-2: Therapeutic Effects of WKYMVm in *E. Coli*-Inoculated Mouse Model

WKYMVm (4 mg/kg) was injected subcutaneously four times into mice 2, 14, 26, and 38 h after peritoneal injection with *E. coli* ($1\times10^9$ cells/mouse). This example also evaluated the therapeutic effects of WKYMVm in other sepsis mouse models. Lethality was reduced in mice inoculated with *E. coli* ($1\times10^9$) and treated subcutaneously with 4 mg/kg WKYMVm four times at 12 h intervals beginning 2 h after inoculation compared to *E. coli*-inoculated mice treated with PBS (FIG. 1e).

1-3. Therapeutic Effects of WKYMVm in LPS Injected Mouse Model

Moreover, WKYMVm also reduced the mortality of mice injected intraperitoneally with 60 mg/kg LPS (FIG. 1f). PBS or WKYMVm (4 mg/kg) was injected subcutaneously four times into mice 2, 14, 26, and 38 h after intraperitoneal injection of 60 mg/kg LPS. Data are expressed as the mean±standard error. *$P<0.05$; $P<0.01$; *$P<0.001$ compared with the vehicle control (a-g). Sample size: n=16-24 (a-e) or n=8 (f,g) mice/group.

COMPARTIVE EXAMPLE 1

Comp 1-1. Therapeutic Effect of WKYMVm on Other FPR Ligands

Because WKYMVm is reported to bind FPR family receptors, the therapeutic effect of other FPR ligands was also evaluated. The therapeutic effect of Trp-Lys-Tyr-Met-Val-Met (WKYMVM) (SEQ ID NO:14) (Baek, S. H., et al., *J.*

*Biol. Chem.* 271:8170-8175), N-formyl-Met-Leu-Phe (fMLF) (SEQ ID NO:15), and MMK-1 peptide (LESI-FRSLLFRVM) (SEQ ID NO: 16) (Klein, C., et al., *Nat. Biotechnol.* 16:1334-1337) was lower than that of WKYMVm (FIG. 1g).

Moreover, the inactive scrambled peptide Val-Trp-Met-Tyr-D-Met-Lys (VWMYmK) (SEQ ID NO:17) had no therapeutic effect (FIG. 1G). FPR-family agonists (WKYMVm (SEQ ID NO:1), WKYMVM(SEQ ID NO:14), fMLF(SEQ ID NO:15) and MMK-1 (SEQ ID NO:16)) or scrambled peptide (VWMYmK: SEQ ID NO: 17) (4 mg/kg, respectively) were injected subcutaneously four times to CLP mice at 2, 14, 26, and 38 h post-CLP.

Comp 1-2. Therapeutic Effect of WKYMVm Analogs

To investigate whether the analogs of WKYMVm(SEQ ID NO:1), WRYMVm(SEQ ID NO: 2), WKWMVm(SEQ ID NO: 3), WKRMVm(SEQ ID NO: 4), WKFMVm(SEQ ID NO: 5), WHYMVm(SEQ ID NO: 6), WKYMYm(SEQ ID NO: 7), WKYMFm(SEQ ID NO: 8), WKYMWm(SEQ ID NO: 9), WKYMVV(SEQ ID NO: 10) and WKEMVm(SEQ ID NO: 11) have therapeutic effects on experimental sepsis, CLP was performed on albino ICR (Institute of Cancer Research) mice, and their survival was monitored for up to 10 days. Within 2 days after CLP, mouse mortality dramatically increased (FIG. 1h). 4 mg/kg of WKYMVm or each analog of WKYMVm was injected subcutaneously four times into CLP mice at 2, 14, 26, and 38 h post-CLP (FIG. 1h).

EXAMPLE 2

Figure 2A:
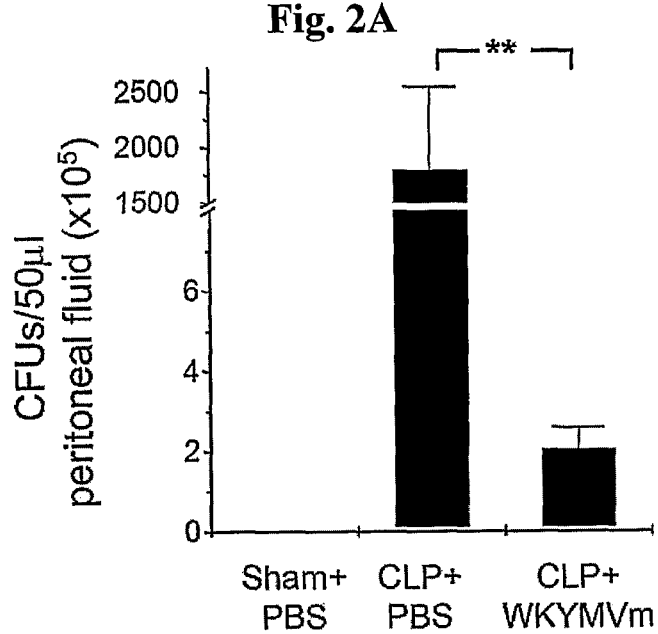
FIGS. 2a to 2d show the effect of WKYMVm on the CLP-induced bacterial colony count, splenocyte death, and lung inflammation.

WKYMVm-Enhanced Survival is Associated with Decrease in Bacterial Colony Counts, Splenocyte Death, and Lung Inflammation 2-1. Bactericidal Activity Because CLP-induced lethality was significantly associated with bacterial colony counts in the peritoneal fluid, the experiment investigated whether FPR activation by WKYMVm affected bacterial clearance from peritoneal fluid. WKYMVm treatment dramatically reduced the intraperitoneal bacterial colony count by 99.8% 24 h after CLP (FIG. 2a). WKYMVm (4 mg/kg) was injected subcutaneously four times into CLP mice 2 and 14 h post-CLP. Peritoneal lavage fluid collected 24 h after sham, CLP or CLP+ WKYMVm administration was cultured overnight on blood-agar base plates at 37° C.; the number of CFUs was then counted.

2-2. Inhibition of Lymphocyte Apoptosis

Figure 2B:
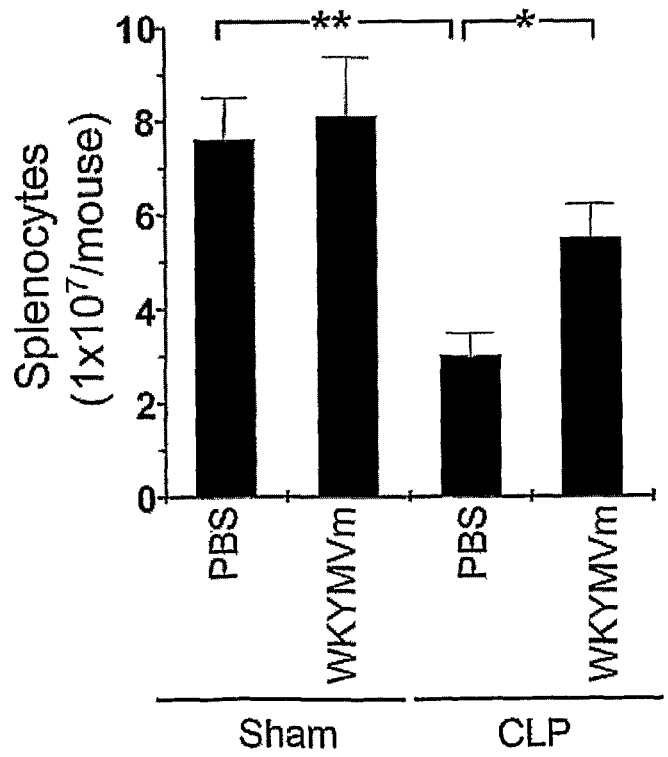

Given the observation that sepsis induces extensive lymphocyte apoptosis (Ayala, A., et al., *Blood.* 87:4261-4275), the experiment also evaluated whether WKYMVm could prevent splenocyte death. Splenocyte death 24 h after CLP was significantly inhibited by WKYMVm treatment (FIG. 2b). WKYMVm (4 mg/kg, subcutaneous) was administered 2 and 14 h after CLP, and the numbers of splenocytes were counted 24 h after CLP in ICR mice.

2-3. Anti-Inflammatory Activity

Figure 2C:
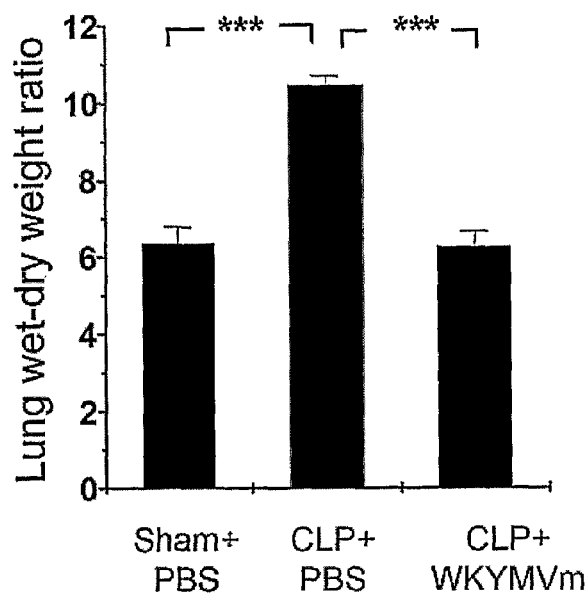

Mortality after sepsis is known to be associated with vital organ inflammation. The inventors found that an indicator of acute lung inflammation, the wet/dry (W/D) weight ratio, was significantly increased in CLP-induced mice treated with PBS, and that this indicator was completely reversed by treatment with WKYMVm (FIG. 2c). The extent of pulmonary edema was quantified by evaluating the W/D weight ratio of the lung as described previously (Liu, D., et al., *Inflamm. Res.* 54:464-470). Whole harvested wet lungs were weighed and then placed in an oven for 48 h at 60° C. The dry weight was then measured and the W/D weight ratio was calculated.

WKYMVm (4 mg/kg, subcutaneous) was administered 2 and 14 h after CLP, and the lungs were used to measure the W/D weight ratio 24 h after CLP in ICR mice. Data are expressed as the mean±standard error (n=16 for a, b; n=5 for c). $*P<0.05$; $P<0.01$; $*P<0.001$. PBS or WKYMVm (4 mg/kg, subcutaneous) was administered 2 h and 14 h after CLP. The mice were sacrificed 24 h after surgery.

Figure 2D:
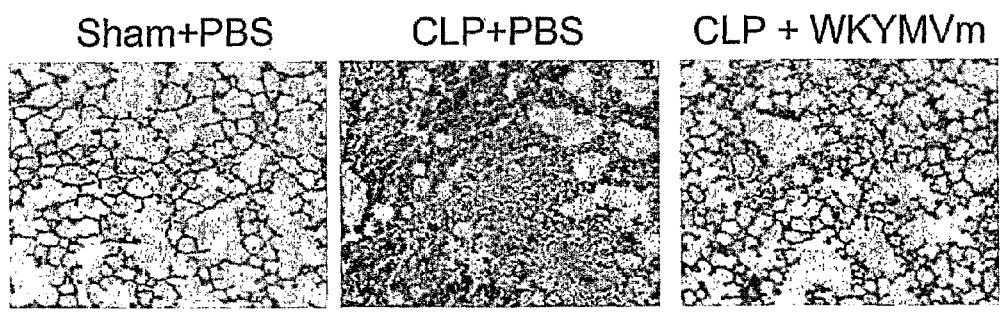

Moreover, histological analyses revealed that CLP-induced lung inflammation was completely reversed by WKYMVm (FIG. 2d). The lungs were stained with hematoxylin and eosin (magnification, ×100). The data are representative of eight mice per group. Mice were subjected to CLP surgery and given PBS or WKYMVm at a dose of 4 mg/kg 2 h later. The mice were euthanized 24 h after surgery, and their lungs were fixed, sectioned, and stained with hematoxylin and eosin for morphological analysis.

EXAMPLE 3

Figure 3A:
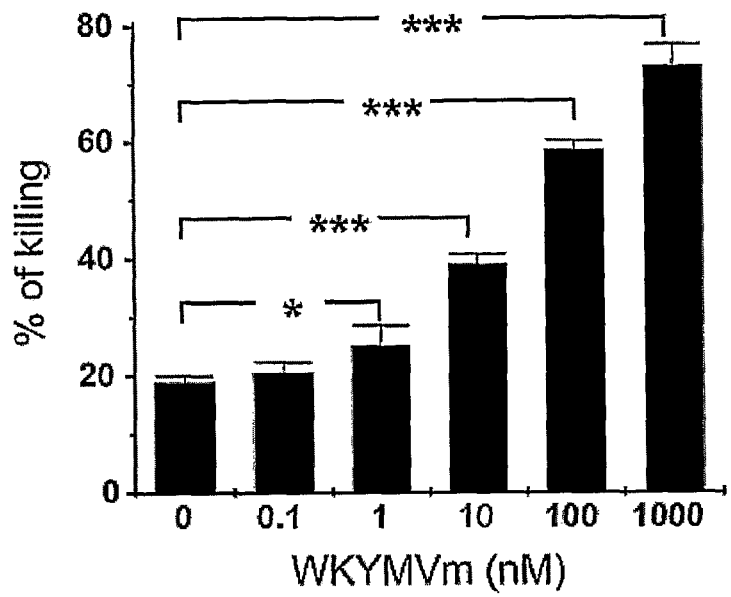
FIGS. 3a to 3e show that WKYMVm enhances bactericidal activity in vitro via $H_2O_2$ production.

WKYMVm Enhances Bacterial Clearance and Hydrogen Peroxide Generation in Phagocytes To determine whether WKYMVm treatment increases bactericidal activity in vitro, mouse neutrophils were allowed to ingest *E. coli* for 1 h and were then stimulated with 0.1-1000 nM WKYMVm for 20 min. Such treatment markedly enhanced the bactericidal activity of the neutrophils in a dose-dependent manner (FIG. 3a). Adherent neutrophils were incubated with $10^6$ opsonized *E. coli* for 1 h, and stimulated with vehicle (PBS) or WKYMVm (0.1, 1, 10, 100, and 1000 nM) for 1 h.

Figure 3B:
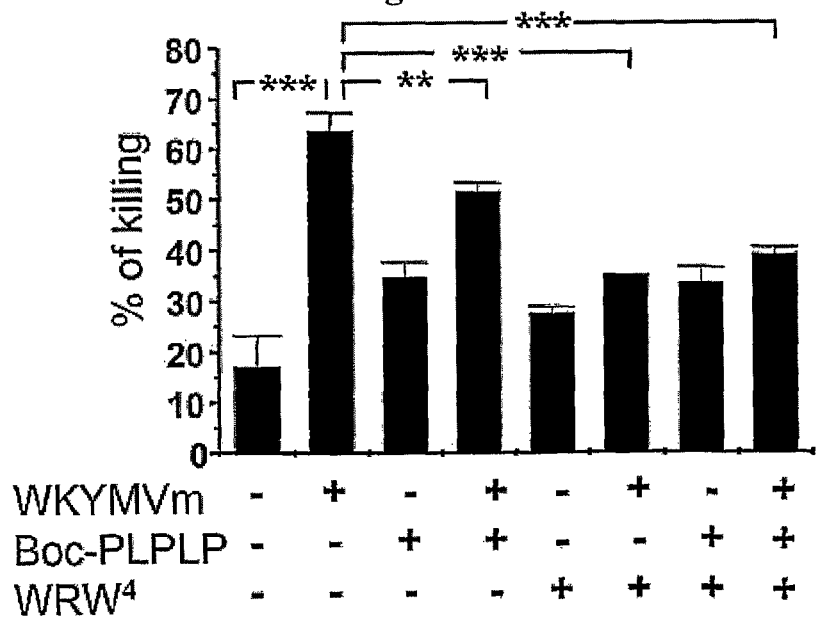

Because FPR1 and FPR2 are expressed in neutrophils (data not shown), this experiment investigated the roles of FPR1-1 and FPR2-mediated pathways in WKYMVm-induced bactericidal activity. Neutrophils pre-treated with Boc-PLPLP or WRW[4] before WKYMVm treatment had significantly inhibited bactericidal activity (FIG. 3b). Mouse neutrophils were isolated from peripheral blood using a Histopaque-1077 solution (Sigma) as described previously (Bae, Y. S., et al., *J. Immunol.* 171:6807-6813, 2003). Boc-PLPLP (10 µM), WRW[4] (10 µM), or Boc-PLPLP (10 µM)+WRW[4] (10 µM) was added 30 min prior to the addition of WKYMVm (100 nM). The number of viable bacteria in the neutrophils was then determined.

Figure 3C:
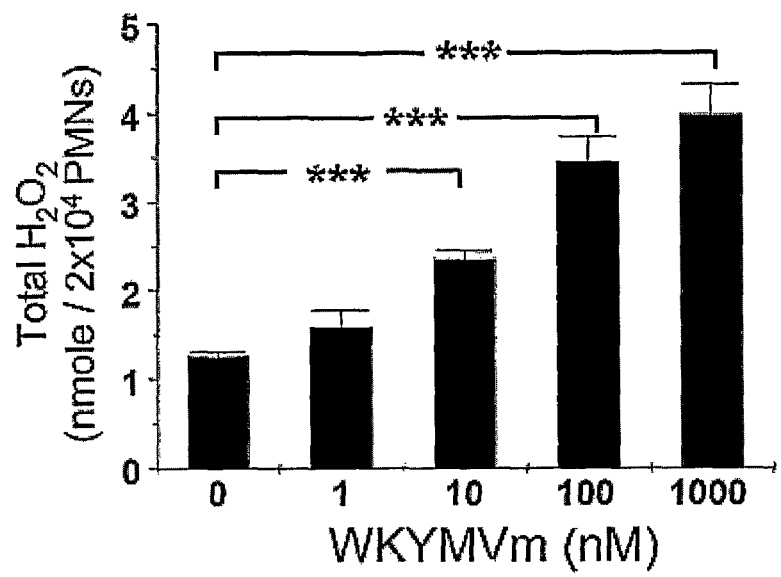

Because the bactericidal effect of phagocytes is related with $H_2O_2$ production (Hampton, M. B., et al., *Blood.* 92:3007-3017), the effect of WKYMVm on $H_2O_2$ generation in mouse neutrophils was evaluated. WKYMVm increased the production of $H_2O_2$ in neutrophils, with a maximal response at 100-1000 nM (FIG. 3c). Mouse neutrophils were stimulated with vehicle (PBS) or WKYMVm (1-1000 nM) for 15 min. Neutrophils isolated from sham, CLP-, or CLP+ WKYMVm-treated mice were stimulated with 100 nM PMA for 1 h. Freshly isolated neutrophils from normal mice were stimulated with various concentrations of WKYMVm for 10 min in the presence of cytochalasin B (5 µM).

To investigate the role of FPR1 and FPR2, neutrophils were preincubated with Boc-PLPLP (10 µM), WRW[4] (10 µM), or vehicle (DMSO) for 30 minutes prior to adding WKYMVm (100 nM) for 10 min. $H_2O_2$ in the supernatant was measured using an $H_2O_2$ assay kit (Molecular Probes).

Figure 3D:
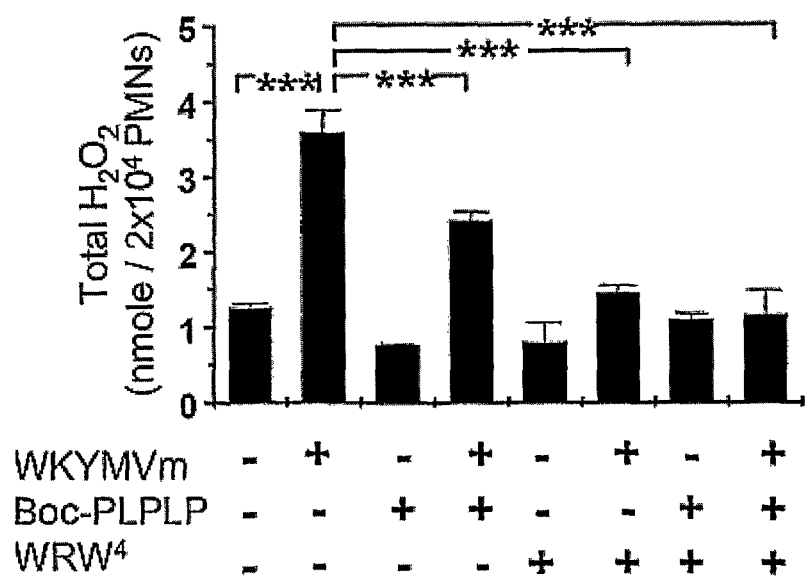

In addition, the effect was partly reversed by pre-treatment with Boc-PLPLP or WRW[4] (FIG. 3d). However, WKYMVm-induced $H_2O_2$ generation was completely reversed by pre-treatment with FPR1+FPR2 antagonists (FIG. 3d). Boc-PLPLP (10 µM), WRW[4] (10 µM), or Boc-PLPLP (10 µM)+ WRW[4] (10 µM) was added 5 min prior to the addition of WKYMVm (100 nM).

Figure 3E:
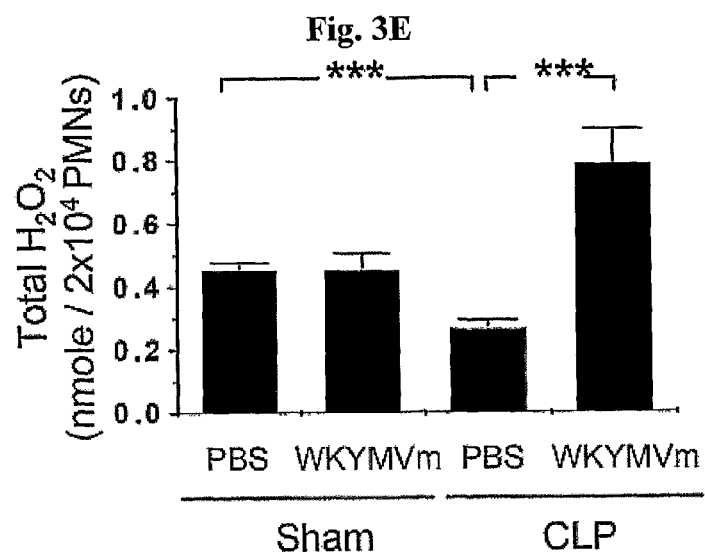

The test found that neutrophils derived from CLP-induced mice failed to produce $H_2O_2$ in response to PMA (FIG. 3e). However, $H_2O_2$ production was significantly enhanced in neutrophils derived from CLP-induced mice treated with WKYMVm compared to without it (FIG. 3e). PBS or WKYMVm (4 mg/kg) was injected subcutaneously four times into CLP mice 2 hr and 14 hr post-CLP. Twenty-four hours after CLP, peritoneal neutrophils were isolated. Neutrophils isolated from sham, CLP, or CLP+WKYMVm mice were stimulated with PMA (100 nM) for 30 min. Data are expressed as the mean±standard error (n=8 for a, b; n=16 for c-e). *P<0.05; P<0.01; *P<0.001.

Neutrophil bactericidal activity was measured according to the method of Yan, J. J., et al., *Nat. Med.* 10:161-167, 2004. Neutrophils were incubated at 37° C. on 13-mm plastic cover slips in 60-mm plastic culture dishes ($1\times10^6$ neutrophils/cover slip) for 1 h. Non-adherent cells were removed with PBS. Adherent neutrophils were incubated with $10^6$ opsonized *E. coli* for 1 h. After washing away the unengulfed *E. coli*, the number of viable bacteria in the neutrophils was determined before and after incubation with several concentrations of WKYMVm or vehicle for 1 h. The percentage of bacteria killed was calculated as 100×(1−number of CFU after WKYMVm stimulation/number of CFU before WKYMVm stimulation). To investigate the role of FPR1 and FPR2, neutrophils were pre-incubated with Boc-PLPLP (10 μM), WRW$^4$ (10 μM), or vehicle (DMSO) for 30 min prior to adding WKYMVm (1 μM) for 1 h.

Following the initial host-microbial interaction, there is widespread activation of the innate immune system, which coordinates a host defensive response. One of the key defense mechanisms involving phagocytes is the elaboration of intracellular toxic mediators such as reactive oxygen species and nitric oxide. The experimental result clearly show that FPR activation by WKYMVm enhanced $H_2O_2$ production, which was associated with enhanced bacterial clearance. FPR1 and FPR2 are known to be receptors for WKYMVm. Antagonists to FPR1 and FPR2 significantly inhibited WKYMVm-induced $H_2O_2$ production in neutrophils. These data suggest that WKYMVm-enhanced survival is related to the bactericidal effect of phagocytes, which is mediated by FPR1 and FPR2. The experimental result also indicates that WKYMVm-enhanced survival is completely dependent upon the FPR2 pathway and only partly dependent on the FPR1 pathway. Thus, WKYMVm has additional effects besides its role in direct bactericidal activity of phagocytes, which may be mediated by FPR2.

EXAMPLE 4

WKYMVm Inhibits CLP-Induced Splenocyte Apoptosis and Enhances Th1 Cell Proliferation in Response to Inert Antigens 4-1. Splenocyte Proliferation Assay in Th1 and Th2 mice To generate the Th1 and Th2 mouse models (FIG. 4b), 6-week-old C57BL/6 WT mice were twice immunized intraperitoneally with 75 μg of OVA+10 μg of LPS or 2 mg of alum on days 0 and 7 and then challenged intraperitoneally with 50 μg of OVA on days 14, 15, and 16. Isolated splenocytes were subjected to a cell proliferation assay with and without OVA incubation. Briefly, splenocytes were harvested in RPMI 1640 media and incubated ($2\times10^5$ cells/well) in 96-well flat-bottom plates at 37° C. for 96 h in medium alone or with 5, 50 or 500 μg OVA/ml. The example measured cellular thymidine incorporation following a 72 h culture period with 1 μCi [$^3$H]thymidine.

Figure 4A:
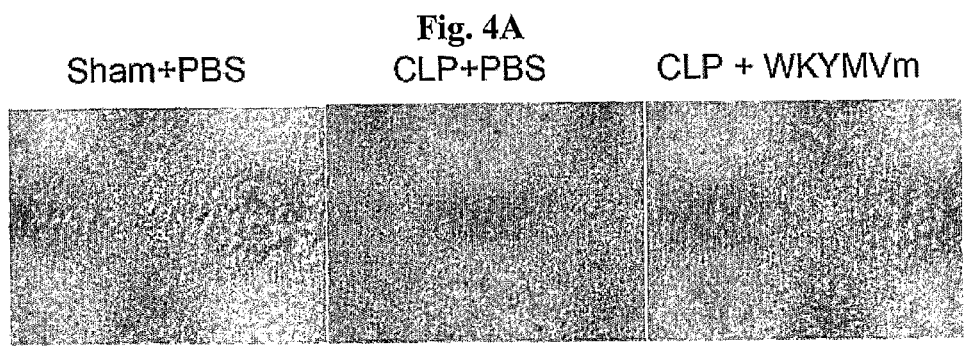
FIGS. 4a to 4f show effect of WKYMVm on CLP-induced splenocyte apoptosis and splenocyte proliferation in response to inert antigens in Th1 and Th2 mouse models.

CLP-induced sepsis caused splenocyte apoptosis; however, this effect was dramatically inhibited by WKYMVm (FIG. 4a). WKYMVm (4 mg/kg) was injected subcutaneously four times into CLP mice 2 and 14 h post-CLP. The spleen, which was collected 24 h after sham, CLP+PBS or CLP+WKYMVm administration, was used for a TUNEL assay (upper) (magnification, ×400). TUNEL-positive cells were counted (lower). A TUNEL assay was performed in paraffin-embedded tissue sections which were first deparaffinized using a standard histological protocol. The sections were then permeabilized with Triton X-100 at 4° C. for 2 min and flooded with TdT enzyme and digoxigenin-dUTP reaction buffer (TUNEL) reagent for 60 min at 37° C. The percentage of apoptotic cells (TUNEL-positive cells) was determined by counting 500 splenocytes under a light microscope.

Figure 4B:
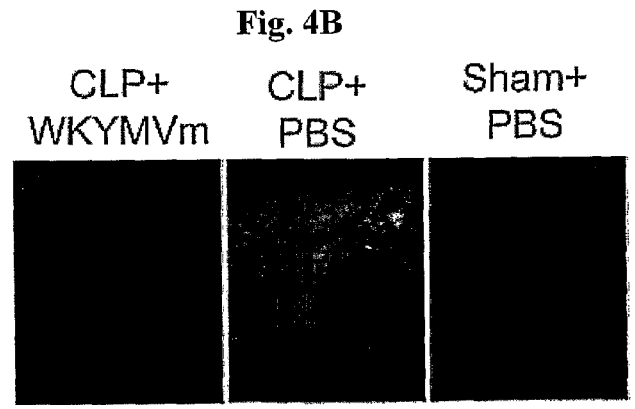

Previous reports demonstrated that lymphocyte apoptosis is mediated by the activation of several critical caspases, including caspase-3 (Hotchkiss, R. S., et al., *Crit. Care Med.* 27:1230-1251, 1999). Similarly, CLP-induced sepsis enhanced the activation of caspase-3, whereas WKYMVm dramatically inhibited it (FIG. 4b). The spleen from the mice described in (a) were used for immunohistochemistry with cleaved-caspase-3 antibody (magnification, ×100). The data are representative of eight mice per group (a, b). This example performed immunohistochemistry in paraffin-embedded tissue sections that were first deparaffinized using a standard histological protocol. After incubation with primary antibodies against cleaved caspase-3 (Cell Signaling), all sections with a fluorochrome-conjugated secondary antibody were stained.

Figure 4C:
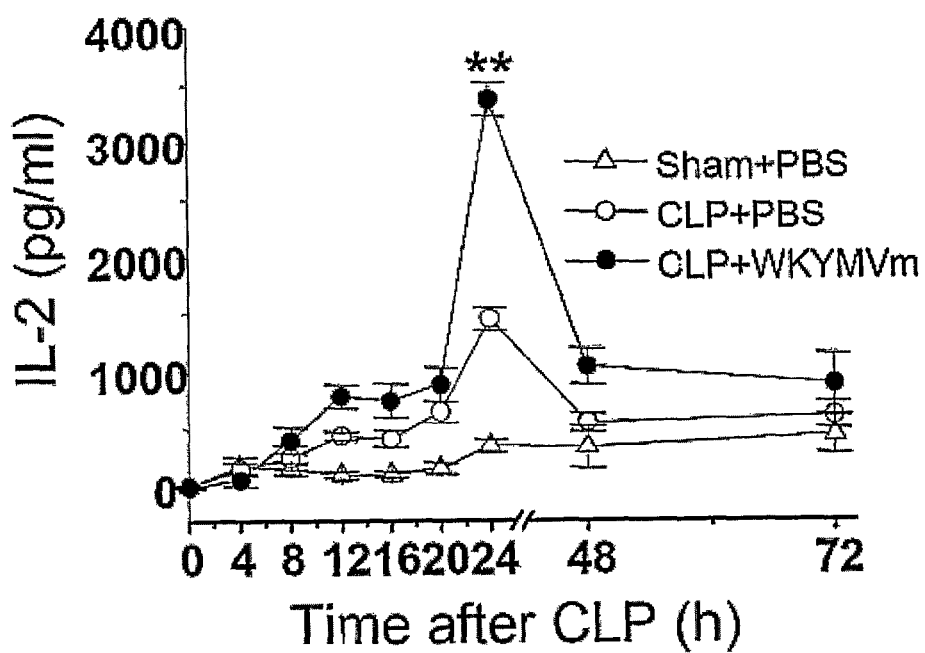
Figure 4D:
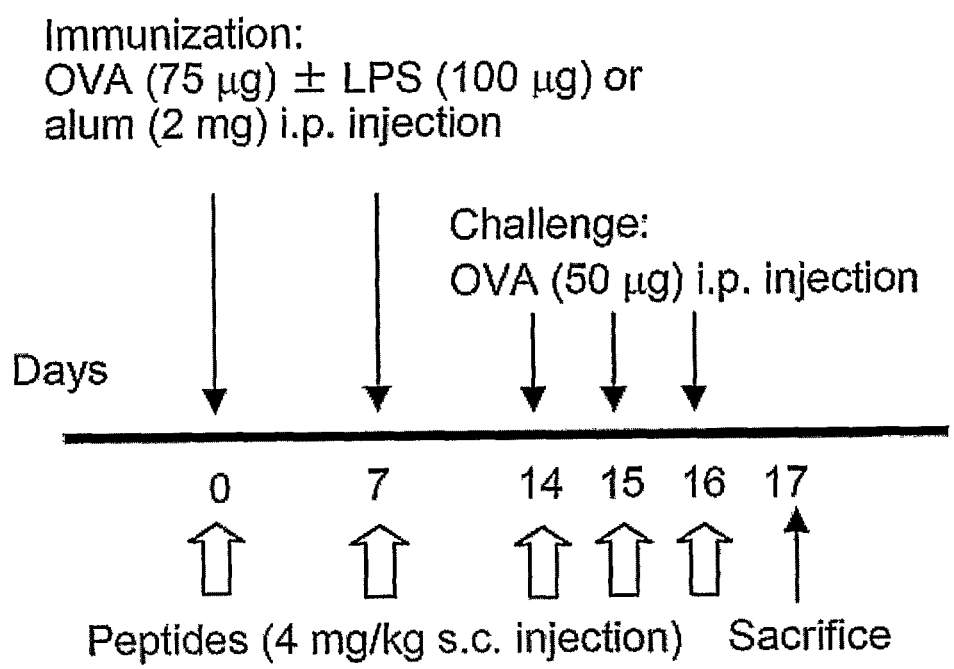

WKYMVm increased the amount of IL-2 in the peritoneal fluid 24 h after CLP (FIG. 4c). Because IL-2 promotes T-cell proliferation (Benczik, M., et al., *Immunol. Invest.* 33:109-142), the effect of FPR activation by WKYMVm on Th1 and Th2 cell proliferation was evaluated using inert antigens. WKYMVm (4 mg/kg) was injected subcutaneously four times into CLP mice 2, 14, 26, and 38 h post-CLP. Separate groups of animals were given sham, CLP+PBS, or CLP+WKYMVm treatment. Data are expressed as the mean±standard error (n=8). *P<0.05; **P<0.01 compared with CLP+PBS. C57BL/6 WT mice were intraperitoneally immunized with OVA in addition to LPS or alum to create Th1 and Th2 cells in the spleen, respectively (FIG. 4d).

Figure 4E:
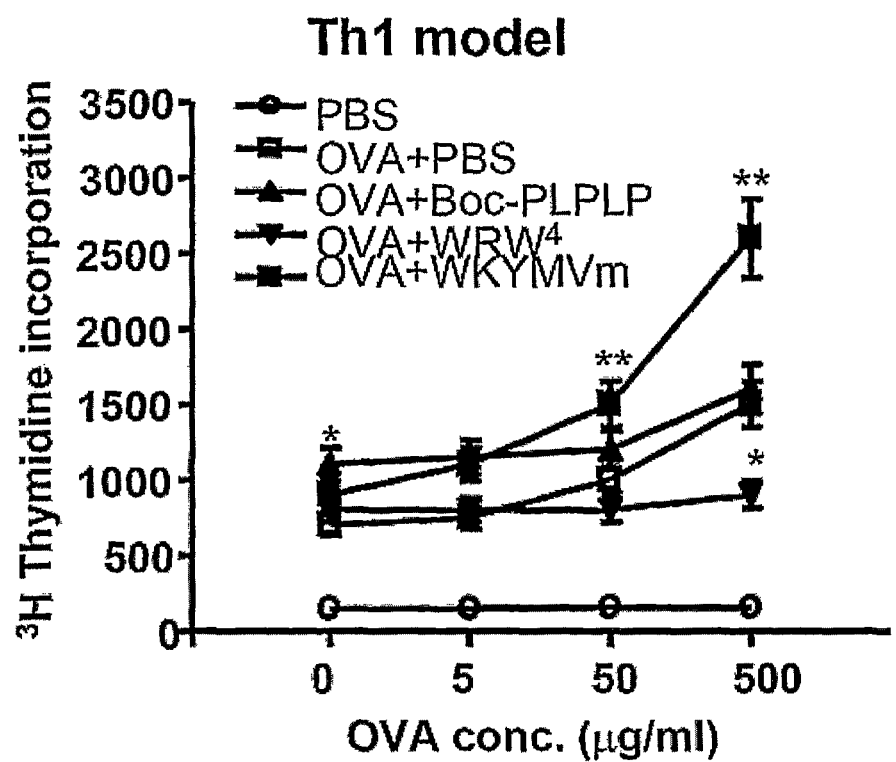
Figure 4F:
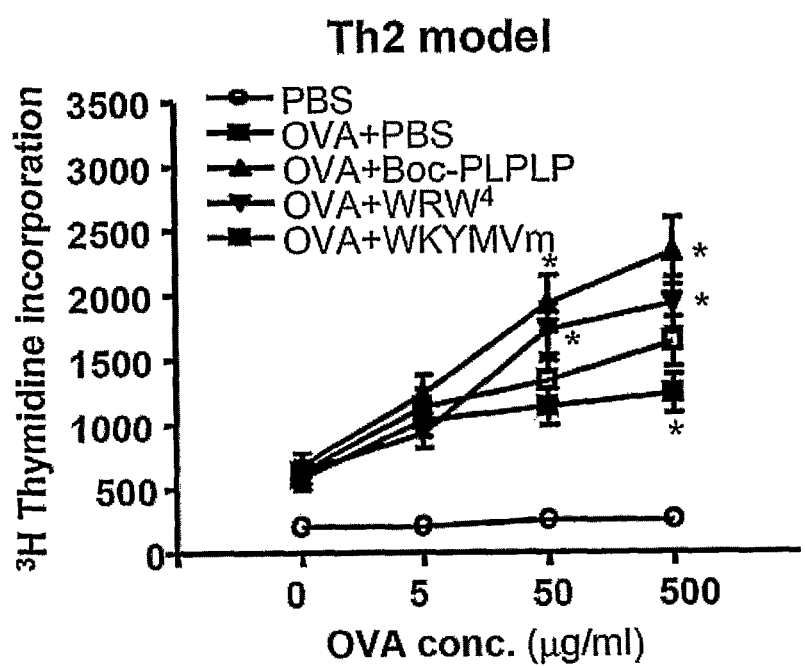

Protocol for the Th1 and Th2 mice (FIG. 4d) was described below. Splenocyte proliferation 72 h after incubation with OVA in mice immunized with OVA+LPS (e) or OVA+alum (f). Data are expressed as the mean±standard error (n=5 for e, f), and * indicates P<0.05 compared to OVA+PBS group; ** indicates P<0.05 versus the other groups. In the Th1 mouse model, splenocyte proliferation was enhanced in WKYMVm-treated mice, but inhibited in Boc-PLPLP- or WRW$^4$-treated mice compared to sham-treated mice after 72 h (FIG. 4e). In contrast, in the Th2 model, splenocyte proliferation was inhibited in WKYMVm-treated mice and enhanced in antagonists-treated mice compared to sham-treated mice after 72 h (FIG. 4f).

EXAMPLE 5

The Effects of WKYMVm are Partly Dependent on an IFN-γ-Mediated Pathway

Figure 5A:
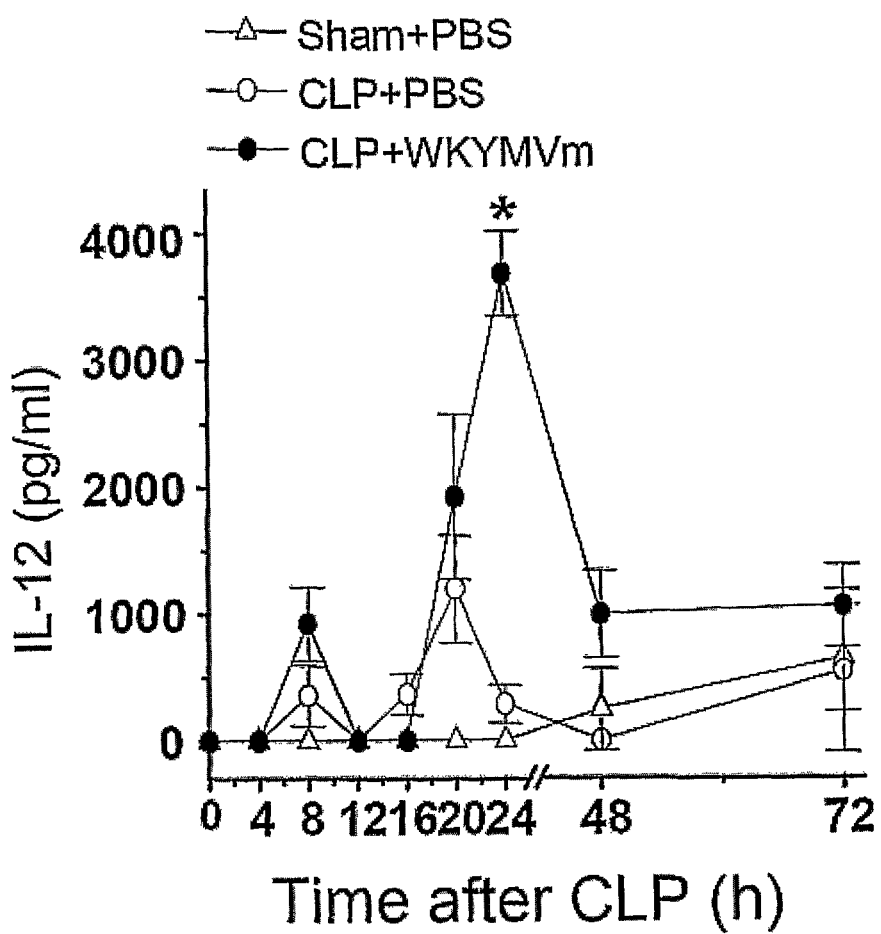
FIGS. 5a to 5g show role of IL-12 and IFN-γ in WKYMVm-induced protection against severe sepsis.
Figure 5B:
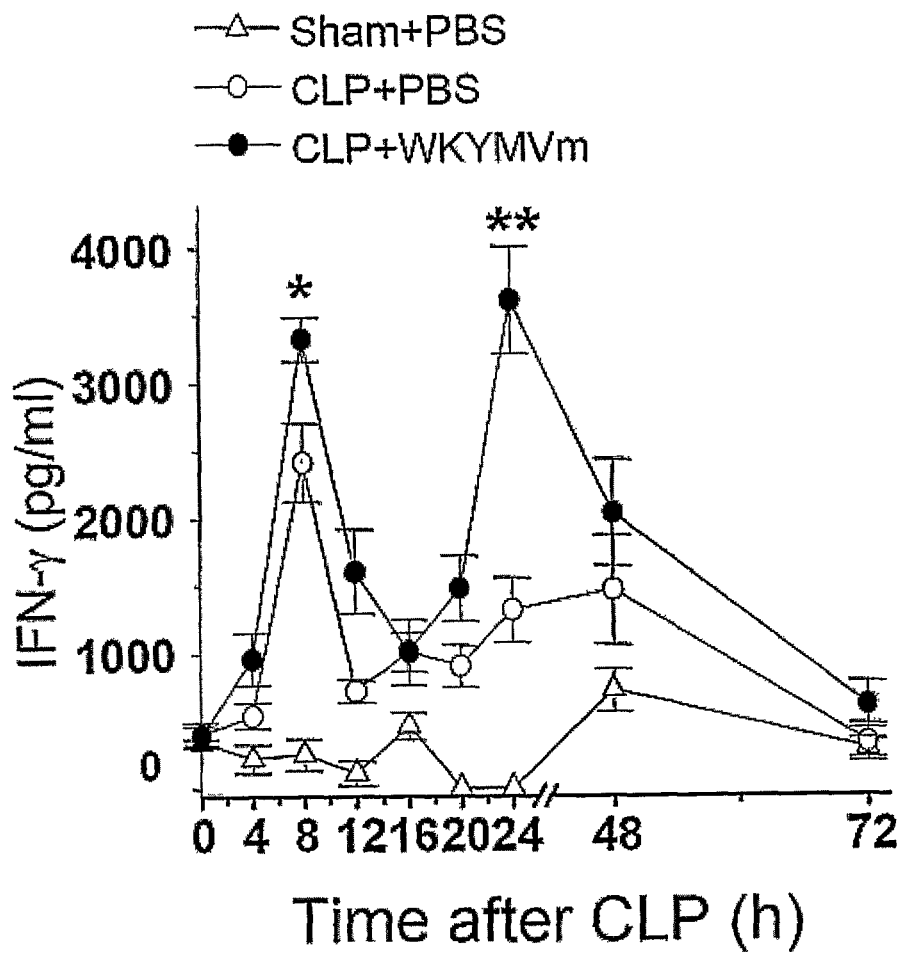

The inventors found that WKYMVm increased the level of IL-12 in the peritoneal fluids 24 h after CLP (FIG. 5a). In contrast, the level of IFN-γ in the peritoneal fluid was increased 8 and 24 h after CLP (FIG. 5b). WKYMVm (4 mg/kg) was injected subcutaneously four times into CLP mice 2, 14, 26, and 38 h post-CLP. Then, and the cytokines present in the peritoneal fluid were measured by ELISA (BD Biosciences Pharmingen).

Separate groups of animals were given sham, CLP+PBS, or CLP+WKYMVm treatment. a, IL-12; b, IFN-γ. Data are expressed as the mean±standard error (n=8 for a, b). *P<0.05; **P<0.01 compared with CLP+PBS. To measure the CLP-induced cytokines in peritoneal lavage fluid, mice were given WKYMVm 2 h, 14 h, 26 h and 38 h after CLP. Peritoneal lavage fluid was collected at various times between 4 h and 72 h after CLP, and the cytokines present in the peritoneal fluid were measured by ELISA (BD Biosciences Pharmingen).

Figure 5C:
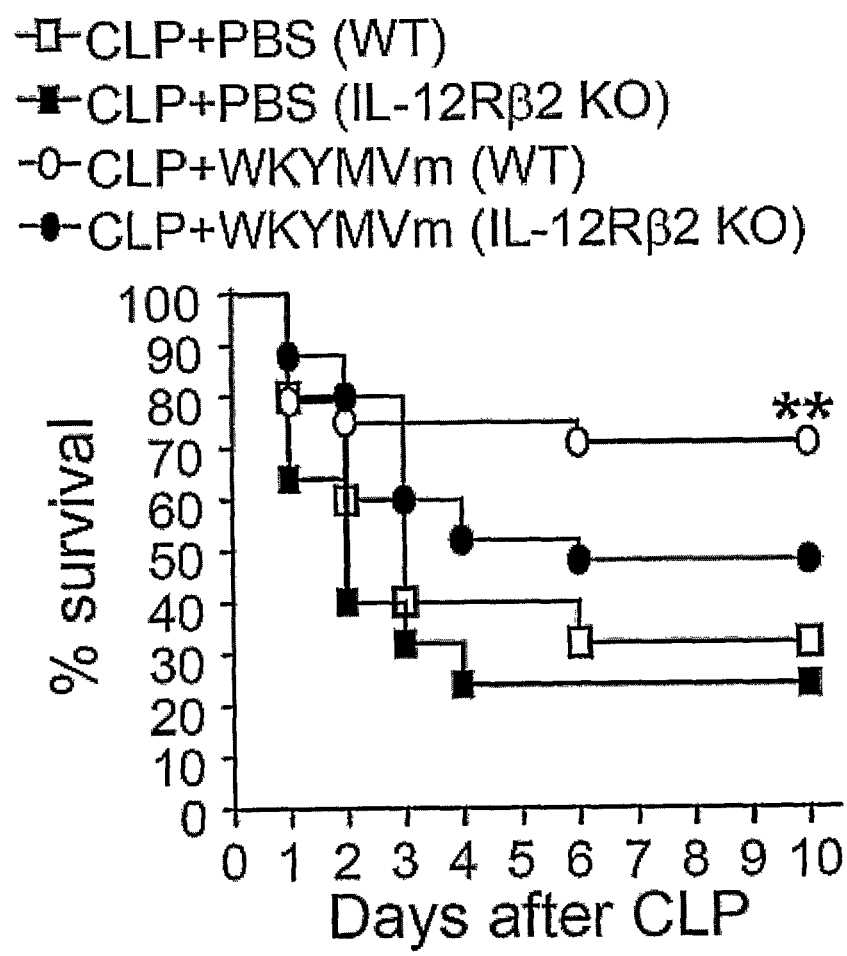
Figure 5D:
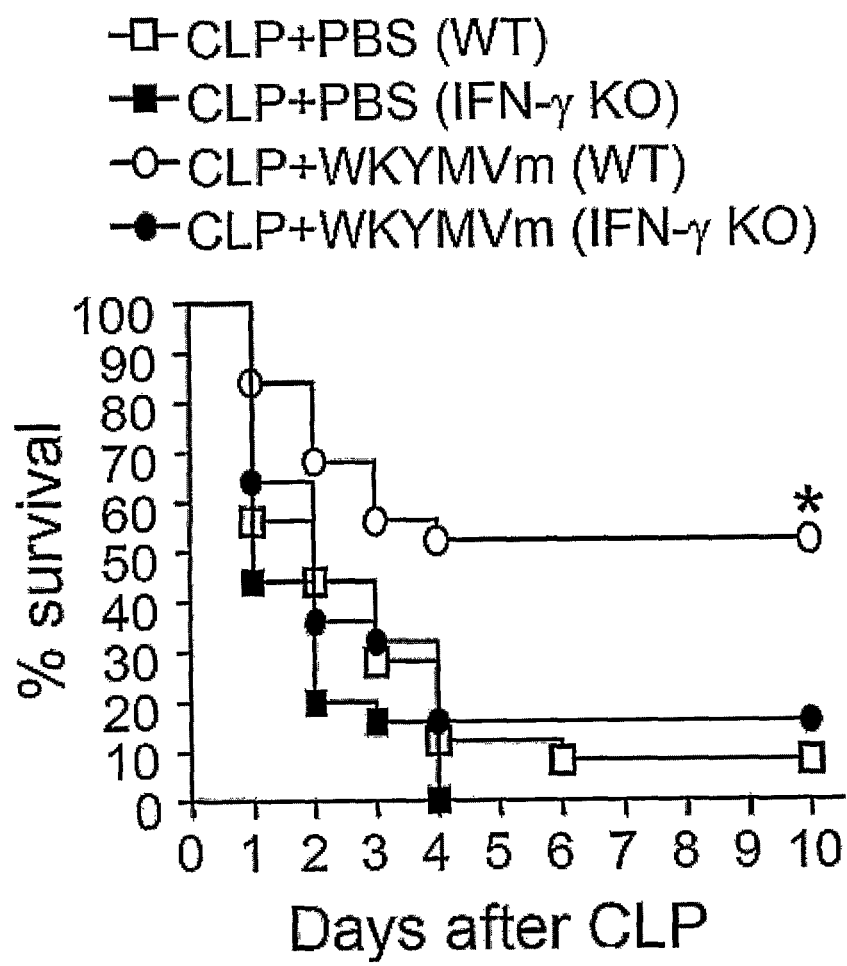

To investigate the role of Th1 cytokines (IL-12 and IFN-γ) on WKYMVm-induced survival effect after sepsis, the CLP model was applied to IL-12Rβ2- and IFN-γ-deficient mice (C57BL/6 background). CLP-induced lethality was significantly decreased in WT C57BL/6 mice treated with WKYMVm (FIG. 5c), but the effect was partly reversed in IL-12Rβ2- and IFN-γ-deficient mice (FIGS. 5c and 5d). WT C57BL/6 or IL-12Rβ2-deficient mice were subcutaneously injected with WKYMVm (4 mg/kg) or PBS four times to CLP mice 2, 14, 26, and 38 h post-CLP. In FIG. 5d, WT C57BL/6 or IFN-γ-deficient mice were subcutaneously injected with WKYMVm (4 mg/kg) or PBS four times to CLP mice 2, 14, 26, and 38 h post-CLP. Data are expressed as the mean±standard error. *P<0.05; **P<0.01 compared with vehicle (c, d). n=10-16 mice per group (c,d)

Figure 5E:
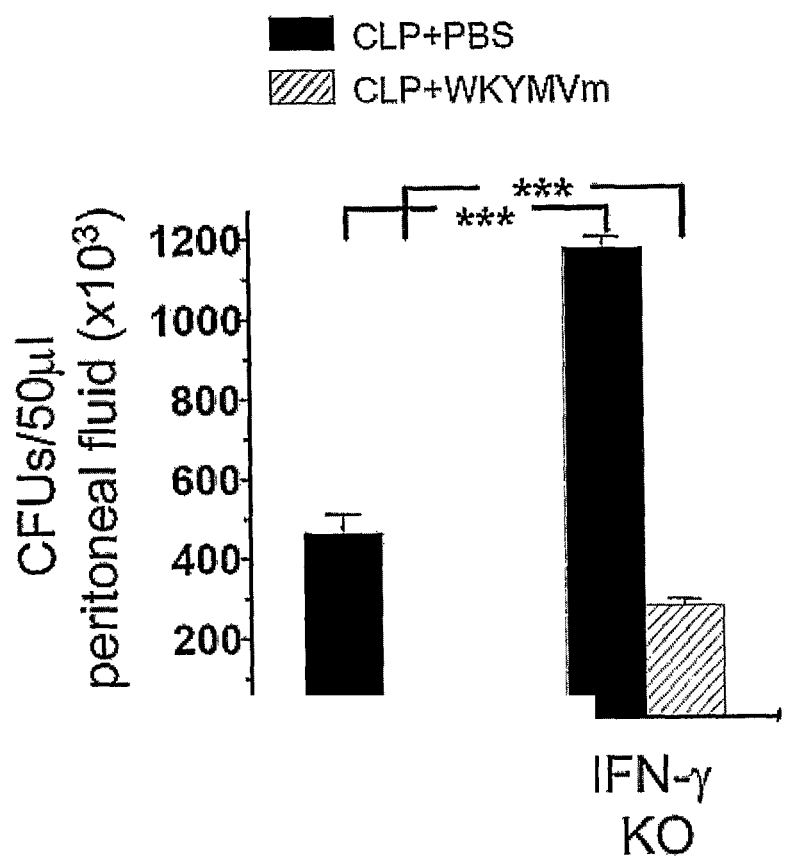

Based on the finding that WKYMVm-induced survival was partly dependent on a Th1 cytokine-mediated pathway, this experiment evaluated whether bactericidal activity, target organ inflammation, and splenocyte apoptosis were also Th1 cytokine-dependent. The bacterial colony counts in peritoneal fluid were higher in CLP-induced IFN-γ-deficient mice treated with WKYMVm than in CLP-induced WT mice treated with WKYMVm (FIG. 5e). WKYMVm (4 mg/kg) was injected subcutaneously four times into CLP mice 2 and 14 h post-CLP. Peritoneal lavage fluid collected 24 h after CLP or CLP+WKYMVm administration was cultured overnight on blood-agar plates at 37° C., and the number of CFUs was counted.

Figure 5F:
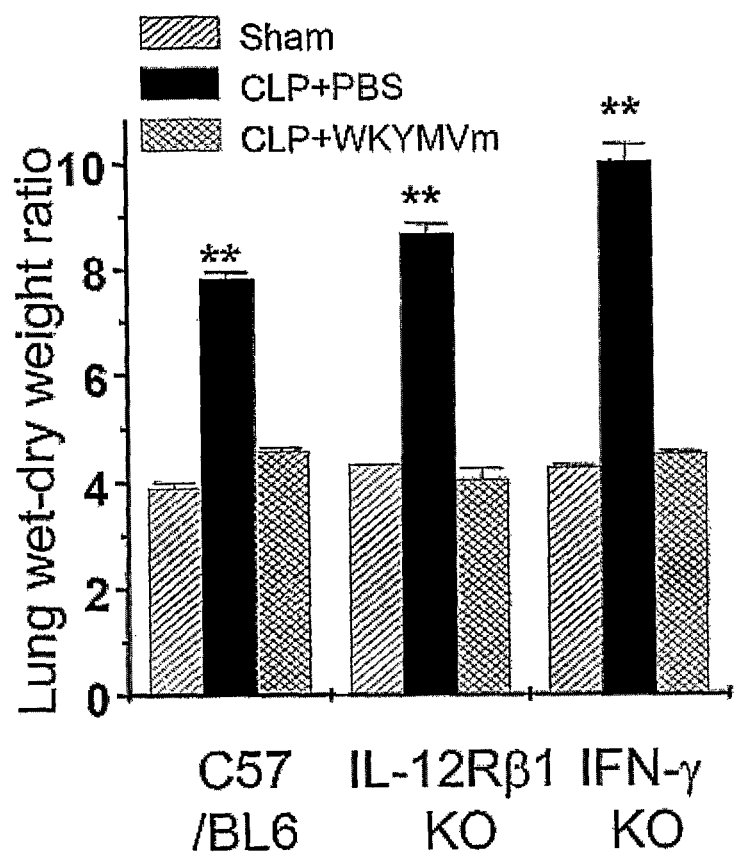
Figure 5G:
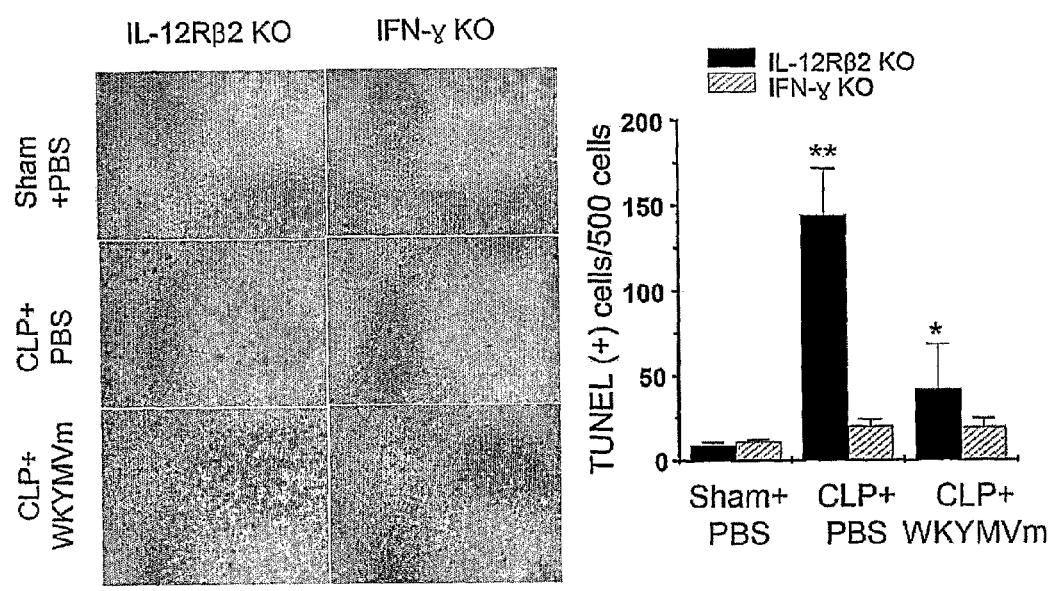

In contrast, W/D weight ratio was higher in CLP-induced WT, IL-12R 2- and IFN-γ-deficient mice treated with PBS, but this effect was completely reversed in CLP-induced WT, IL-12Rβ2- and IFN-γ-deficient mice treated with WKYMVm (FIG. 5f). Lungs were used to measure the W/D weight ratio 24 h after CLP in C57BL/6, IL-12Rβ2-deficient and IFN-γ-deficient mice. Interestingly, CLP-induced splenocyte apoptosis was not observed in IFN-γ-deficient mice, though it was induced by CLP and reversed by WKYMVm in IL-12Rβ2-deficient mice (FIG. 5g). WKYMVm (4 mg/kg) was injected subcutaneously four times into CLP mice 2 and 14 h post-CLP. The spleen, which was collected 24 h after sham, CLP or CLP+WKYMVm administration, was used for a TUNEL assay (left) (magnification, Δ400). The number of TUNEL-positive cells was counted (right). Data are expressed as the mean±standard error. *P<0.05; P<0.01; *P<0.001. (n=8 for e-g).

Following severe sepsis, there is an increase in the level of Th2 cytokines and a decrease in the level of Th1 cytokines that may result in impaired cellular immunity (Kox, W. J., et al., *Intensive Care Med.* 26:S124-S128, 2000). Therapies designed to augment the production of Th1 cytokines may thus be beneficial in the treatment of severe sepsis after peritonitis. IFN-γ is secreted by Th1 cells and by innate immune cells, such as natural killer cells and macrophages (Trinchieri, G. *Curr. Opin. Immunol.* 9:17-23, 1997). The properties of IFN-γ for defense against microbes include the stimulation of phagocyte bactericidal activity, the stimulation of antigen presentation through class I and class II MHC molecules, and the orchestration of leukocyte-endothelium interactions (Dighe, A. S., et al., *Immunity.* 3:657-666, 1995). Severe sepsis down-regulates IFN-γ production (Kox, W. J., *Intensive Care Med.* 26:S124-S128, 2000). A clinical study demonstrated that recombinant IFN-γ-treated septic patients showed an improved clinical course (Kox, W. J., et al., *Arch. Intern. Med.* 157:389-393, 1997). The data indicate increased IFN-γ production due to FPR activation with WKYMVm in a sepsis mouse model. Moreover, FPR activation enhanced Th1 cell proliferation but inhibit Th2 cell proliferation to inert antigens. In contrast, the effect of FPR activation was partly reversed in IFN-γ-deficient mice. The survival effect was positively associated with the bacterial colony counts in IFN-γ-deficient mice. This suggests that the survival and bactericidal effects of FPR activation depend in part on IFN-γ production following FPR activation.

EXAMPLE 6

The Anti-Inflammatory Effect of WKYMVm is Directly Related to the Down-Regulation of Pro-Inflammatory Cytokines Mouse neutrophils ($3 \times 10^6$ cells/0.3 ml) were placed in RPMI 1640 medium containing 5% FBS in 24-well plates and kept in a 5% $CO_2$ incubator at 37° C. The neutrophils were then incubated with LPS (100 ng/ml) for 3 and 6 h, respectively, in the presence or absence of WKYMVm (0.1 and 1 μM). LPS (100 ng/ml) was added to the cells 30 min later, and cell-free supernatants were collected, centrifuged, and measured for IL-1β or TNF-α by ELISA (BD Biosciences Pharmingen) according to the manufacturer's instruction.

Figure 6A:
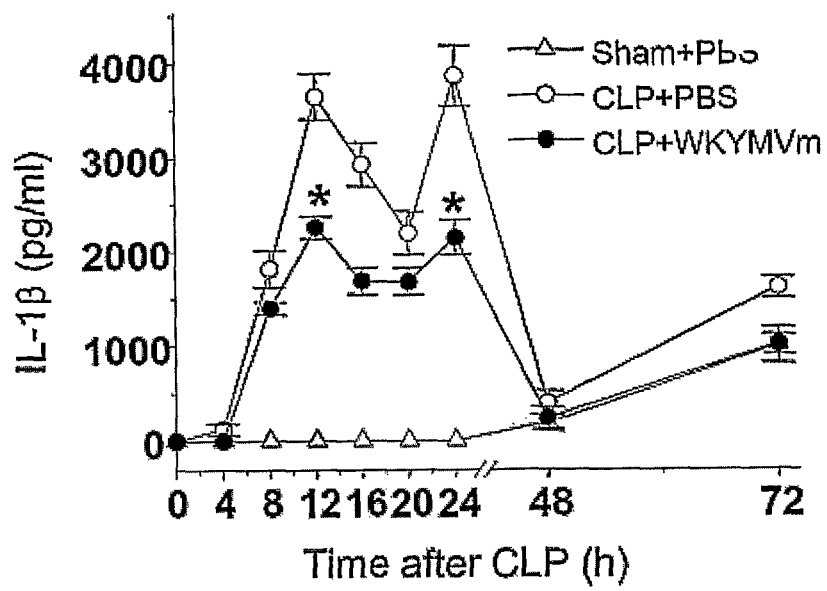
FIGS. 6a to 6d show the role of WKYMVm in the production of inflammatory cytokines
Figure 6B:
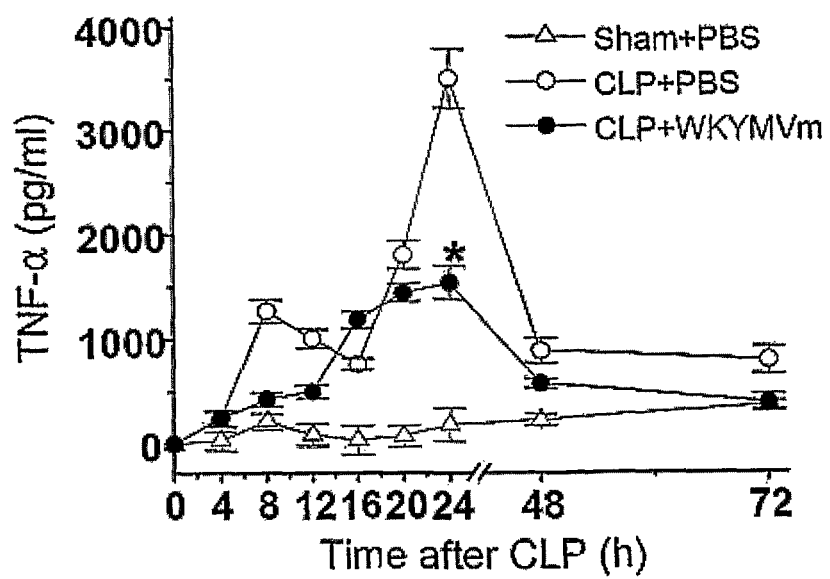

The levels of the pro-inflammatory cytokines IL-1β and TNF-γ were significantly decreased in the peritoneal fluid of CLP-induced WT mice treated with WKYMVm (FIGS. 6a and 6b). WKYMVm (4 mg/kg) was injected subcutaneously four times into CLP mice 2, 14, 26, and 38 h post-CLP. Separate groups of animals were subjected to sham, CLP+PBS, or CLP+WKYMVm treatment. a, IL-1β; b, TNF-α. Data are expressed as the mean±standard error (n=8). *P<0.05 compared with CLP+PBS (a,b)

Figure 6C:
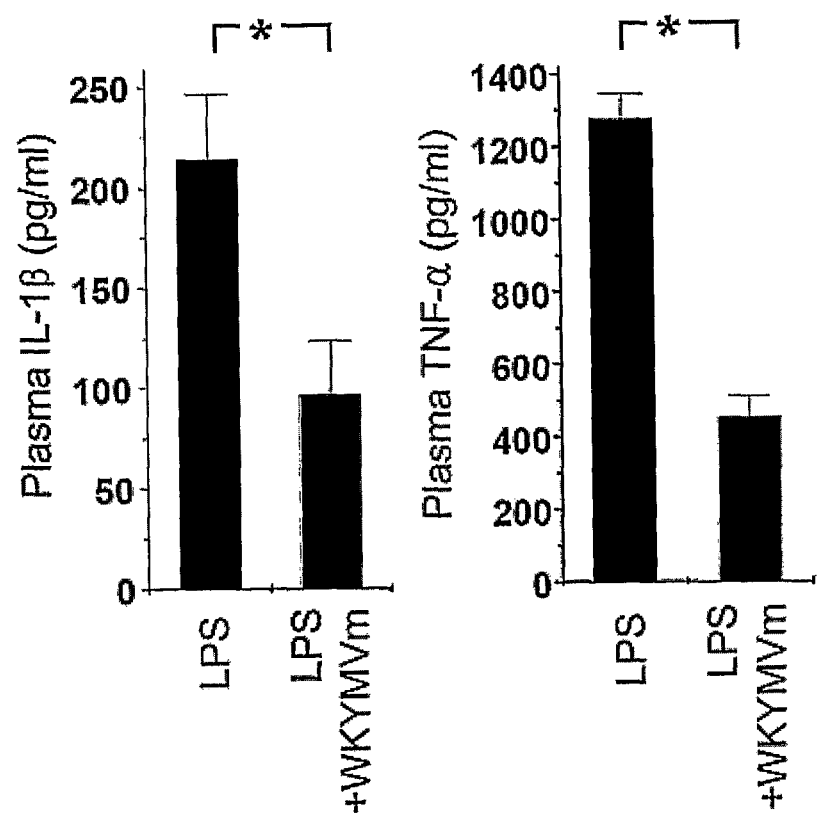

To evaluate whether this down-regulation was caused by a direct inhibitory effect of WKYMVm on pro-inflammatory cytokine production, the in vivo production of pro-inflammatory cytokines was measured following intraperitoneal application of 60 mg/kg LPS. The plasma levels of IL-1β and TNF-α 4 h after LPS administration were significantly decreased in mice treated with 4 mg/kg WKYMVm compared to mice treated with PBS (FIG. 6c). WKYMVm (4 mg/kg) was injected subcutaneously into mice 2 h after intraperitoneal injection of 60 mg/kg LPS; Plasma was collected 4 h later. The plasma levels of IL-1β and TNF-α were measured.

Figure 6D:
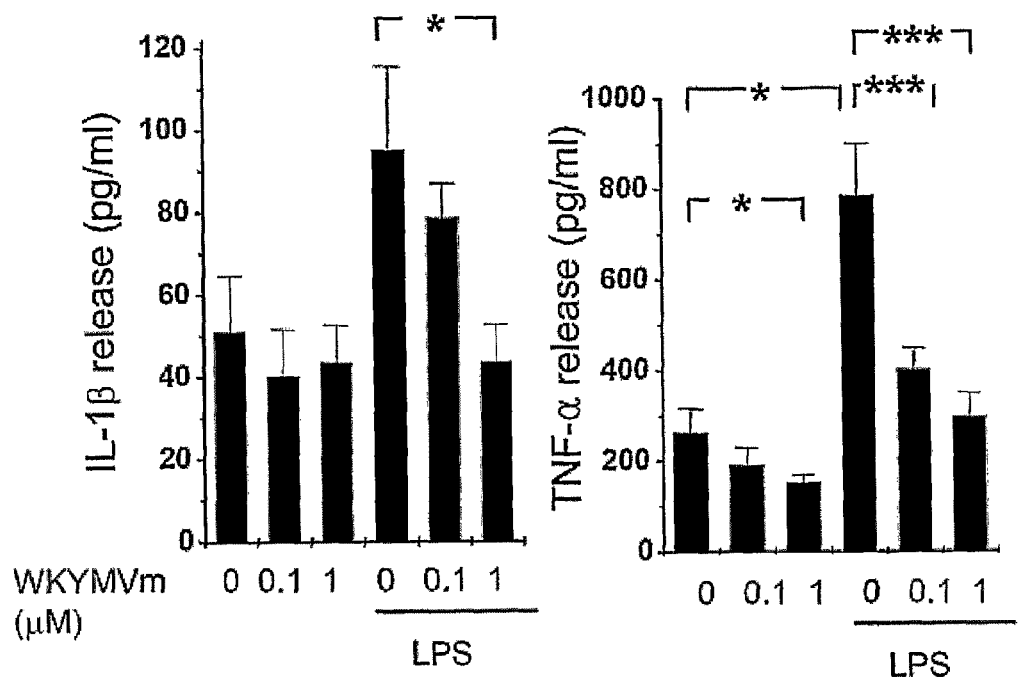

Moreover, the in vitro release of LPS-induced IL-1β and TNF-α from mouse neutrophils was inhibited by WKYMVm treatment in a dose-dependent manner (FIG. 6d). Mouse neutrophils were pre-incubated with PBS or WKYMVm (0.1 and 1 μM) for 30 min and then stimulated with PBS or LPS (100 ng/ml) for 3 h. The levels of IL-1β and TNF-α were measured by ELISA (d). Data are presented as the mean±standard error (n=16 for c, d). *P<0.05; ***P<0.001.

The down-regulation of immunity that accompanies sepsis is related to the development of lymphocyte apoptosis; thus, the inhibition of sepsis-induced lymphocyte apoptosis is a good therapeutic target. Indeed, FPR activation by WKYMVm inhibited apoptosis of immune cells in the spleen. Recent evidence suggests that IFN-γ induces apoptosis in antigen-specific Th1 cells in the spleen (Berner, V., et al., *Nat. Med.* 13:354-360, 2007). The experimental data also indicate that immune cell apoptosis in the spleen is IFN-γ-dependent. These findings suggest that the treatment of sepsis with recombinant IFN-γ induces adverse effects that compromise the therapeutic effect of IFN-γ, and that FPR activation by WKYMVm may be a superior therapeutic approach.

Many innate immune responses to infection can, under some circumstances, cause cell and tissue damage leading to multiple organ failure (the clinical hallmark of severe sepsis). The recognition of microbial molecules by tissue phagocytes triggers the production or release of pro-inflammatory mediators that increase blood flow to infected tissues, enhance the permeability of local blood vessels, and recruit inflammatory cells to the site of infection. The results indicate that FPR activation by WKYMVm inhibits the CLP-induced production of several pro-inflammatory cytokines including IL-1β and TNF-γ, which is associated with vital organ dysfunction due to acute inflammation. Moreover, experiments in vitro and in vivo demonstrate that FPR activation inhibits LPS-induced pro-inflammatory cytokine production. These findings suggest that the FPR activation exerts its therapeutic effects by preventing acute inflammation via the direct inhibition of pro-inflammatory cytokine production. This indicates that FPR activation by WKYMVm may be superior to blocking individual pro-inflammatory mediators in the treatment of sepsis.

EXAMPLE 7

Figure 7A:
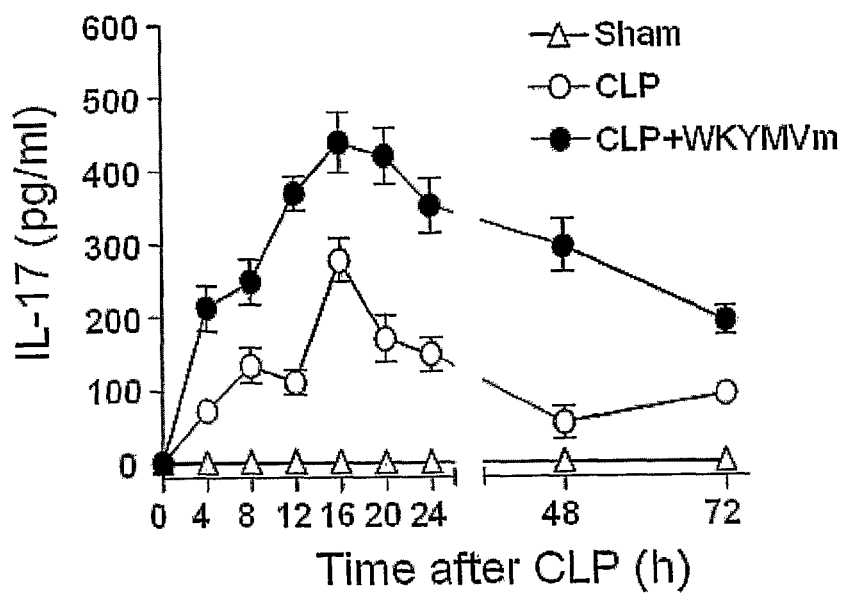
FIGS. 7a to 7e show that the anti-inflammatory effects of WKYMVm are dependent on an IL-17-mediated pathway.
Figure 7B:
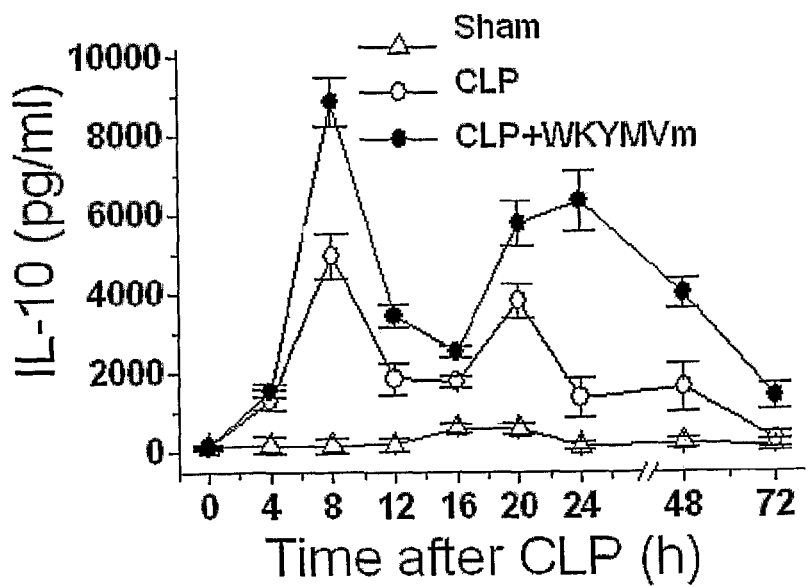
Figure 7C:
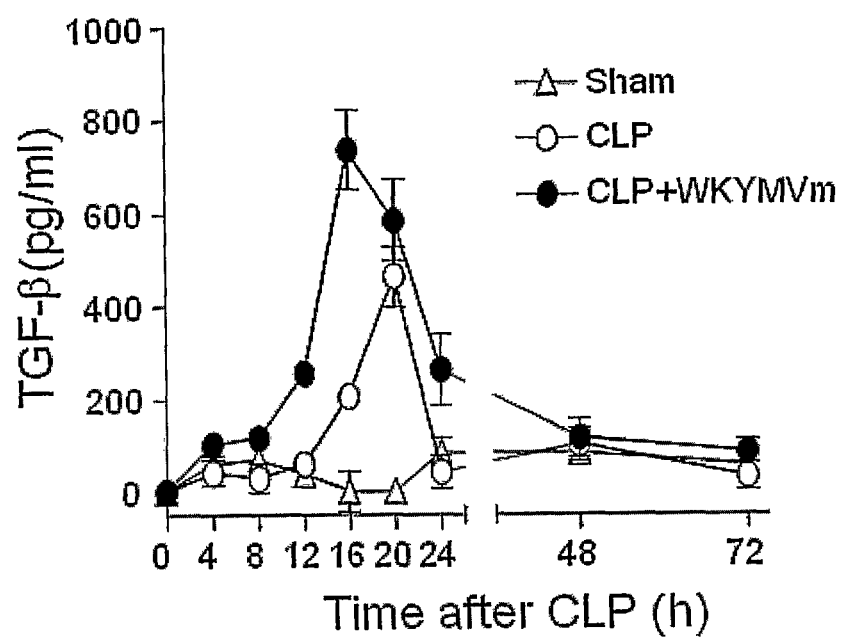
Figure 7D:
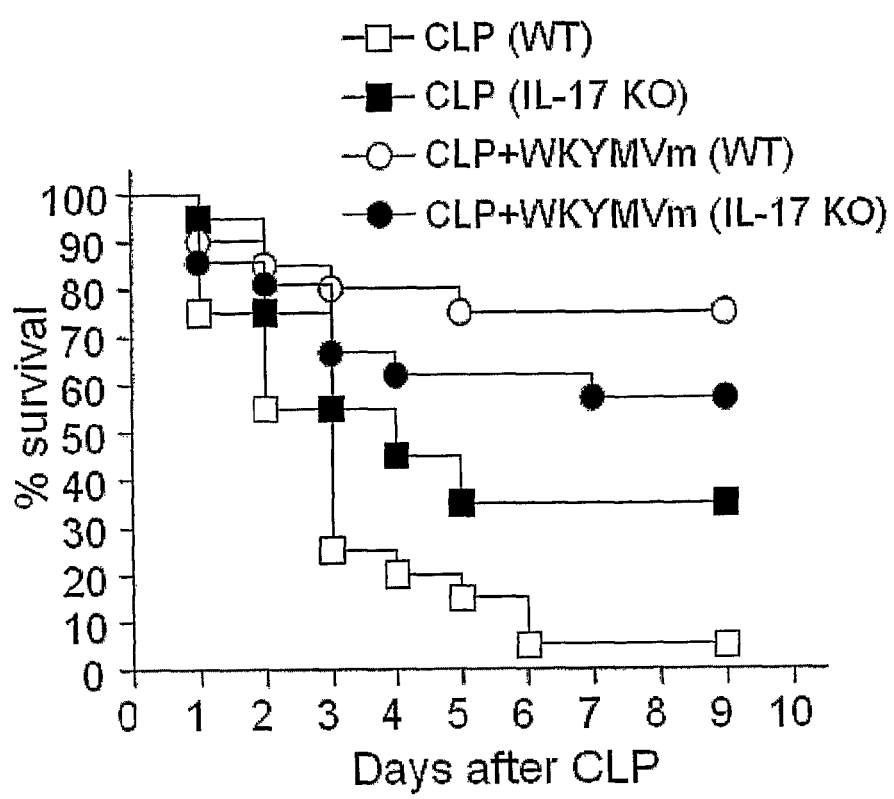
Figure 7E:
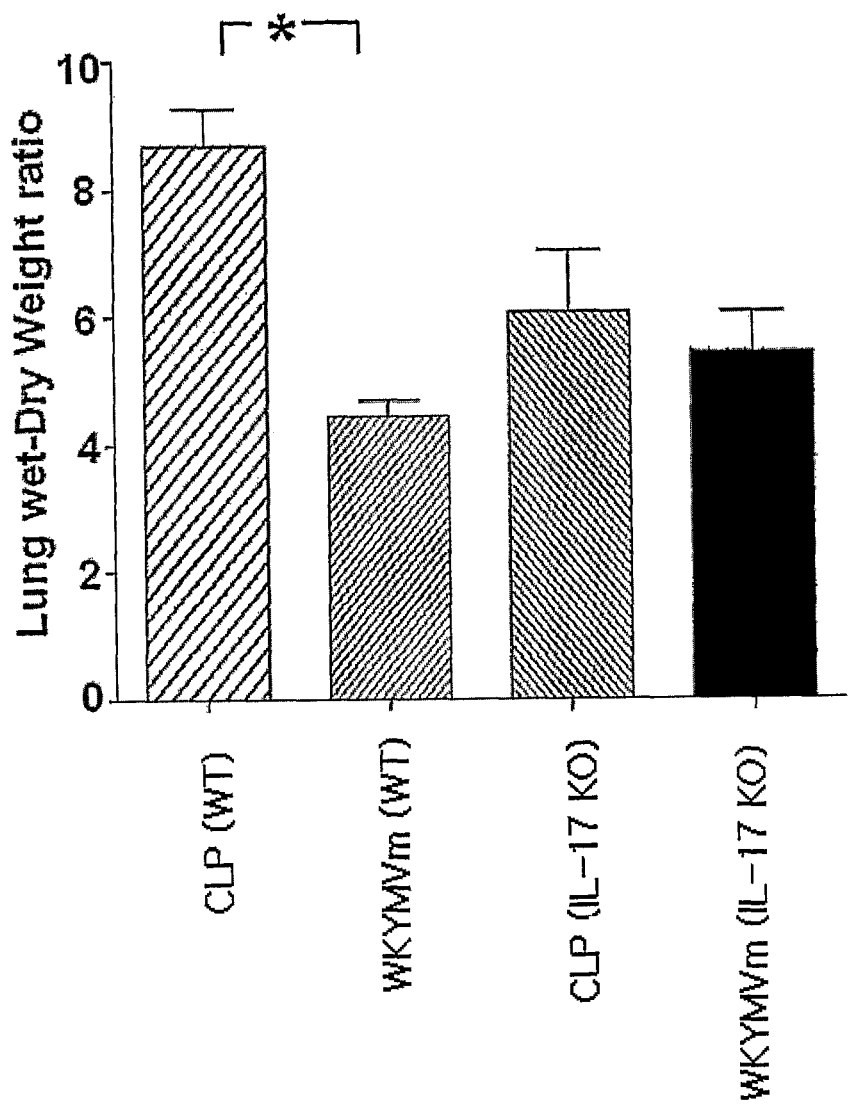

The Anti-Inflammatory Effects of WKYMVm are Dependent on an IL-17-Mediated Pathway WKYMVm increased the level of IL-17 in the peritoneal fluids as early as 4 hrs after CLP (FIG. 7a). Administration of WKYMVm also increased the IL-10 and TGF- from 8 and 12 hrs after CLP, respectively (FIGS. 7b and 7c). To investigate the role of IL-17 on the enhanced survival effect by FPR activation, the CLP model was applied to IL-17-deficient and WT control mice (C57BL/6 background). This study showed that the enhanced survival by WKYMVm treatment was partly reversed in IL-17-deficient mice (FIG. 7d). In terms of the role of IL-17 on the anti-inflammatory effects of FPR activation, lung W/D weight ratio inhibited by WKYMVm in WT mice was not observed in IL-17-deficient mice (FIG. 7e).

What is claimed is:

1. A method of regulating immune response in a subject comprising administering to said subject an immunoregulating agent comprising a peptide consisting of the amino acid sequence of SEQ ID NO:1 in a therapeutically effective amount, wherein the peptide decreases expression of inflammatory cytokine which is Interleukin-1β (IL-1β), Tumor necrosis factor-α (TNF-α), or Interleukin-6 (IL-6) and increases expression of Th1 cytokine which is Interferon-γ (IFN-γ), Interleukin-2 (IL-2), or Interleukin-12 (IL-12).

2. The method of regulating immune response according to claim 1, wherein the peptide binds and activates Formylpeptide receptor 1 (FPR 1) or Formylpeptide receptor 2 (FPR 2) in mouse.

3. The method of regulating immune response according to claim 1, wherein the peptide binds and activates FPR, FPRL1 or FPRL2 in human.

4. The method of regulating immune response according to claim 1, wherein the peptide increases the expression of Interleukin-17 (IL-17).

5. The method of regulating immune response according to claim 1, wherein the peptide increases the expression of anti-inflammatory cytokine which is Transforming growth factor-α(TGF- α) or Interleukin-10 (IL-10).

6. The method of regulating immune response according to claim 1, wherein the regulation of immune response is involved in anti-inflammatory reaction, an antibacterial reaction, or an inhibition of an immune cell apoptosis.

7. The method of regulating immune response according to claim 1, wherein the regulation of immune response is involved in the inhibition of the reduction of splenocyte or thymocyte derived by severe sepsis.

8. The method of regulating immune response according to claim 1, wherein the regulation of immune response is involved in prevention or treatment of severe sepsis or Acute respiratory distress syndrome (ARDS) and the peptide is administered in an amount of 0.0064 to 6.4 mg/kg-day.

9. The method of regulating immune response according to claim 8, wherein the peptide is administered in an amount of 0.064 to 0.64 mg/kg-day.

10. The method of regulating immune response according to claim 1, wherein the peptide is administered orally or paraenterally.

\* \* \* \* \*

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: WKYMVm
<220> FEATURE:
<221> NAME/KEY: MOD_RES
<222> LOCATION: (6)
<223> OTHER INFORMATION: D-Met

<400> SEQUENCE: 1

Trp Lys Tyr Met Val Met
 1               5

<210> SEQ ID NO 2
<211> LENGTH: 6
<212> TYPE: PRT
<213> ORGANISM: Artificial Sequence
<220> FEATURE:
<223> OTHER INFORMATION: WRYMVm
<220> FEATURE:
<221> NAME/KEY: MOD_RES
<222> LOCATION: (6)
<223> OTHER INFORMATION: D-Met

<400> SEQUENCE: 2

Trp Arg Tyr Met Val Met
 1               5

<210> SEQ ID NO 3
<211> LENGTH: 6
<212> TYPE: PRT
<213> ORGANISM: Artificial Sequence
<220> FEATURE:
<223> OTHER INFORMATION: WKWMVm
<220> FEATURE:
<221> NAME/KEY: MOD_RES
<222> LOCATION: (6)
<223> OTHER INFORMATION: D-Met

<400> SEQUENCE: 3
```

Trp Lys Trp Met Val Met
1               5

<210> SEQ ID NO 4
<211> LENGTH: 6
<212> TYPE: PRT
<213> ORGANISM: Artificial Sequence
<220> FEATURE:
<223> OTHER INFORMATION: WKRMVm
<220> FEATURE:
<221> NAME/KEY: MOD_RES
<222> LOCATION: (6)
<223> OTHER INFORMATION: D-Met

<400> SEQUENCE: 4

Trp Lys Arg Met Val Met
1               5

<210> SEQ ID NO 5
<211> LENGTH: 6
<212> TYPE: PRT
<213> ORGANISM: Artificial Sequence
<220> FEATURE:
<223> OTHER INFORMATION: WKFMVm
<220> FEATURE:
<221> NAME/KEY: MOD_RES
<222> LOCATION: (6)
<223> OTHER INFORMATION: D-Met

<400> SEQUENCE: 5

Trp Lys Phe Met Val Met
1               5

<210> SEQ ID NO 6
<211> LENGTH: 6
<212> TYPE: PRT
<213> ORGANISM: Artificial Sequence
<220> FEATURE:
<223> OTHER INFORMATION: WHYMVm
<220> FEATURE:
<221> NAME/KEY: MOD_RES
<222> LOCATION: (6)
<223> OTHER INFORMATION: D-Met

<400> SEQUENCE: 6

Trp His Tyr Met Val Met
1               5

<210> SEQ ID NO 7
<211> LENGTH: 6
<212> TYPE: PRT
<213> ORGANISM: Artificial Sequence
<220> FEATURE:
<223> OTHER INFORMATION: WKYMYm
<220> FEATURE:
<221> NAME/KEY: MOD_RES
<222> LOCATION: (6)
<223> OTHER INFORMATION: D-Met

<400> SEQUENCE: 7

Trp Lys Tyr Met Tyr Met
1               5

<210> SEQ ID NO 8
<211> LENGTH: 6
<212> TYPE: PRT
<213> ORGANISM: Artificial Sequence
<220> FEATURE:
<223> OTHER INFORMATION: WKYMFm

```
<220> FEATURE:
<221> NAME/KEY: MOD_RES
<222> LOCATION: (6)
<223> OTHER INFORMATION: D-Met

<400> SEQUENCE: 8

Trp Lys Tyr Met Phe Met
 1               5

<210> SEQ ID NO 9
<211> LENGTH: 6
<212> TYPE: PRT
<213> ORGANISM: Artificial Sequence
<220> FEATURE:
<223> OTHER INFORMATION: WKYMWm
<220> FEATURE:
<221> NAME/KEY: MOD_RES
<222> LOCATION: (6)
<223> OTHER INFORMATION: D-Met

<400> SEQUENCE: 9

Trp Lys Tyr Met Trp Met
 1               5

<210> SEQ ID NO 10
<211> LENGTH: 6
<212> TYPE: PRT
<213> ORGANISM: Artificial Sequence
<220> FEATURE:
<223> OTHER INFORMATION: WKYMVV

<400> SEQUENCE: 10

Trp Lys Tyr Met Val Val
 1               5

<210> SEQ ID NO 11
<211> LENGTH: 6
<212> TYPE: PRT
<213> ORGANISM: Artificial Sequence
<220> FEATURE:
<223> OTHER INFORMATION: WKEMVm
<220> FEATURE:
<221> NAME/KEY: MOD_RES
<222> LOCATION: (6)
<223> OTHER INFORMATION: D-Met

<400> SEQUENCE: 11

Trp Lys Glu Met Val Met
 1               5

<210> SEQ ID NO 12
<211> LENGTH: 5
<212> TYPE: PRT
<213> ORGANISM: Artificial Sequence
<220> FEATURE:
<223> OTHER INFORMATION: FPR1 Antagonist
<220> FEATURE:
<221> NAME/KEY: MOD_RES
<222> LOCATION: (1)
<223> OTHER INFORMATION: N-t-butoxycarbonyl

<400> SEQUENCE: 12

Phe Leu Phe Leu Phe
 1               5

<210> SEQ ID NO 13
<211> LENGTH: 6
<212> TYPE: PRT
<213> ORGANISM: Artificial Sequence
```

```
<220> FEATURE:
<223> OTHER INFORMATION: FPR2 antagonist

<400> SEQUENCE: 13

Trp Arg Trp Trp Trp Trp
 1               5

<210> SEQ ID NO 14
<211> LENGTH: 6
<212> TYPE: PRT
<213> ORGANISM: Artificial Sequence
<220> FEATURE:
<223> OTHER INFORMATION: WKYMVM

<400> SEQUENCE: 14

Trp Lys Tyr Met Val Met
 1               5

<210> SEQ ID NO 15
<211> LENGTH: 3
<212> TYPE: PRT
<213> ORGANISM: Artificial Sequence
<220> FEATURE:
<223> OTHER INFORMATION: N-formyl-Met-Leu-Phe
<220> FEATURE:
<221> NAME/KEY: MOD_RES
<222> LOCATION: (1)
<223> OTHER INFORMATION: N-formyl

<400> SEQUENCE: 15

Met Leu Phe
 1

<210> SEQ ID NO 16
<211> LENGTH: 13
<212> TYPE: PRT
<213> ORGANISM: Artificial Sequence
<220> FEATURE:
<223> OTHER INFORMATION: MMK-1 peptide

<400> SEQUENCE: 16

Leu Glu Ser Ile Phe Arg Ser Leu Leu Phe Arg Val Met
 1               5                  10

<210> SEQ ID NO 17
<211> LENGTH: 6
<212> TYPE: PRT
<213> ORGANISM: Artificial Sequence
<220> FEATURE:
<223> OTHER INFORMATION: Inactive scrambled peptide
<220> FEATURE:
<221> NAME/KEY: MOD_RES
<222> LOCATION: (5)
<223> OTHER INFORMATION: D-Met

<400> SEQUENCE: 17

Val Trp Met Tyr Met Lys
 1               5
```